(12) United States Patent
Vollmers et al.

(10) Patent No.: US 10,280,449 B2
(45) Date of Patent: May 7, 2019

(54) METHODS OF PRODUCING NUCLEIC ACID LIBRARIES AND COMPOSITIONS AND KITS FOR PRACTICING SAME

(71) Applicant: The Regents of the University of California, Oakland, CA (US)

(72) Inventors: Christopher Vollmers, Santa Cruz, CA (US); Charles Cole, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/738,955

(22) PCT Filed: Jun. 28, 2016

(86) PCT No.: PCT/US2016/039891
§ 371 (c)(1),
(2) Date: Dec. 21, 2017

(87) PCT Pub. No.: WO2017/004083
PCT Pub. Date: Jan. 5, 2017

(65) Prior Publication Data
US 2018/0179579 A1    Jun. 28, 2018

Related U.S. Application Data

(60) Provisional application No. 62/186,152, filed on Jun. 29, 2015.

(51) Int. Cl.
*C12Q 1/6806* (2018.01)
*C12Q 1/6869* (2018.01)
*C40B 40/08* (2006.01)
*C12N 15/10* (2006.01)

(52) U.S. Cl.
CPC ....... *C12Q 1/6806* (2013.01); *C12N 15/1093* (2013.01); *C12Q 1/6869* (2013.01); *C40B 40/08* (2013.01)

(58) Field of Classification Search
None
See application file for complete search history.

(56) References Cited

U.S. PATENT DOCUMENTS

2014/0031261 A1    1/2014    Goryshin et al.

FOREIGN PATENT DOCUMENTS

| WO | 2009049889 | 4/2009 | |
|---|---|---|---|
| WO | 2010048605 | 4/2010 | |
| WO | WO-2012061832 A1 * | 5/2012 | ......... C12N 15/1065 |
| WO | 2012103154 | 8/2012 | |
| WO | WO-2013177220 A1 * | 11/2013 | ........... C12Q 1/6874 |
| WO | 2014142850 | 9/2014 | |
| WO | 2015094861 | 6/2015 | |

OTHER PUBLICATIONS

Head et al. (2014) "Library Construction for Next-generation Sequencing: Overviews and Challenges" Biotechniques. 56(2):6-7. doi:10.2144/000114133.

* cited by examiner

*Primary Examiner* — Tracy Vivlemore
*Assistant Examiner* — Sahana S Kaup
(74) *Attorney, Agent, or Firm* — Brian E. Davy; Bozicevic, Field & Francis LLP

(57) ABSTRACT

Aspects of the present disclosure include methods of producing nucleic acid libraries. In certain aspects, the methods include producing tagged primer extension products, and contacting aliquots of the tagged primer extension products with transposomes to produce tagged extension product fragments. The methods may further include sequencing the tagged extension products and tagged extension product fragments to determine the sequences of nucleic acids of interest. Also provided are compositions and kits that find use, e.g., in practicing embodiments of the methods.

11 Claims, 15 Drawing Sheets
Specification includes a Sequence Listing.

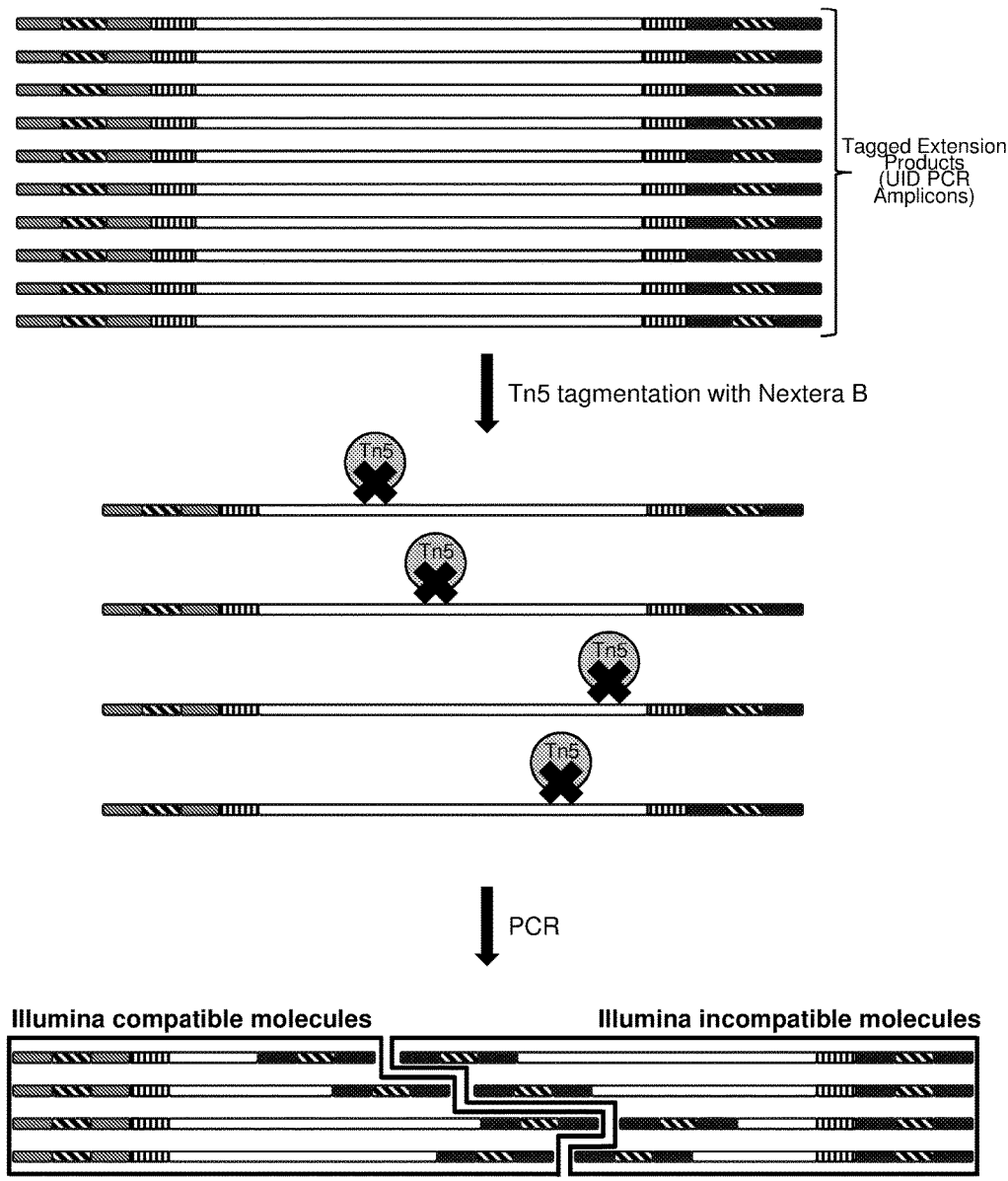

FIG. 1 (cont'd)
G
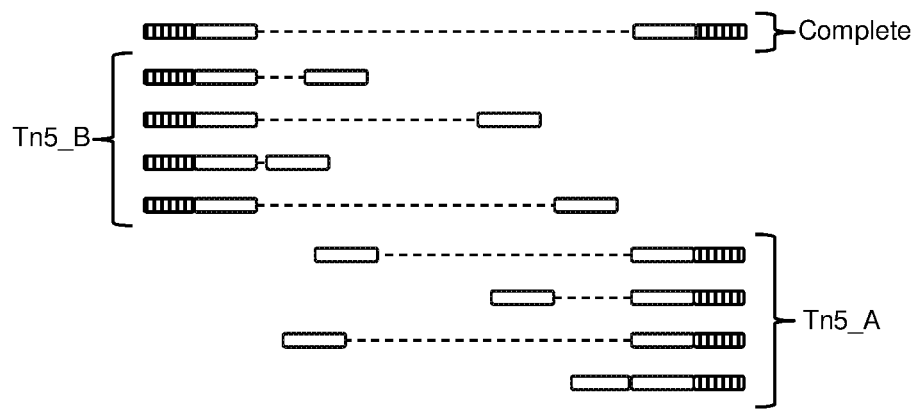
Assembly
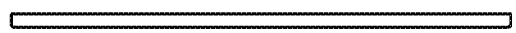
Annotation

FIG. 3

| Sequencing Type | Uncut | | | Tn5_A | | | Tn5_B | | |
|---|---|---|---|---|---|---|---|---|---|
| | Raw Reads | Trimmed Reads (2) | Filtered (3) Raw Reads | Trimmed Reads (2) | Matched to IGH Molecule (4) | Raw Reads | Trimmed Reads (2) | Matched to IGH Molecule (4) |
| 1 L1 MiSeq 2x300 (1) | 20,208 | 17,458 | 13,368 | 69,843 | 68,497 | 45,011 | 34,548 | 34,149 | 23,202 |
| 2 L2 HiSeq3000 2x150 | 632,862 | 616,455 | 419,806 | 721,170 | 499,054 | 361,991 | 772,119 | 665,771 | 310,626 |
| 2 L3 HiSeq3000 2x150 | 487,734 | 472,524 | 324,440 | 579,863 | 386,223 | 299,358 | 561,434 | 278,939 | 225,852 |
| 2 L3 HiSeq3000 2x150 | 433,838 | 418,516 | 291,178 | 528,636 | 342,389 | 263,776 | 550,731 | 263,902 | 219,531 |
| 2 L4 HiSeq3000 2x150 | 557,106 | 540,536 | 346,380 | 693,041 | 467,540 | 355,386 | 902,579 | 536,693 | 282,460 |
| 2 L5 HiSeq3000 2x150 | 354,157 | 344,655 | 217,515 | 416,839 | 365,942 | 216,773 | 517,037 | 263,368 | 185,432 |
| 2 L6 HiSeq3000 2x150 | 638,250 | 614,355 | 415,119 | 710,034 | 461,150 | 362,823 | 822,053 | 389,669 | 320,769 |
| 2 L7 HiSeq3000 2x150 | 683,842 | 635,338 | 450,934 | 871,653 | 275,950 | 210,611 | 518,966 | 273,540 | 331,770 |
| 2 L8 HiSeq3000 2x150 | 974,320 | 876,862 | 607,219 | 1,076,387 | 530,996 | 455,907 | 970,972 | 422,766 | 259,640 |

| IGH molecule groups | IGH molecule groups with Tn5_A and Tn5_B reads | IGH molecule groups with Tn5_A but no Tn5_B reads | IGH molecule groups with Tn5_B but no Tn5_A reads | IGH molecule groups without Tn5_A and Tn5_B reads | IGH molecule groups with >1 uncut raw reads | Assembled IGH Molecules (5) | Annotated IGH molecules (6) |
|---|---|---|---|---|---|---|---|
| 6,278 | 5,681 | 454 | 141 | 39 | 3,808 | 2,709 | 2,715 |
| 63,174 | 19,010 | 15,526 | 11,062 | 23,574 | 16,680 | 15,424 | 15,162 |
| 72,484 | 21,815 | 13,986 | 10,840 | 26,043 | 27,763 | 16,597 | 16,346 |
| 55,445 | 14,446 | 10,960 | 10,735 | 20,221 | 17,395 | 13,216 | 13,027 |
| 67,362 | 16,012 | 16,017 | 9,282 | 25,451 | 23,873 | 16,985 | 16,850 |
| 38,065 | 12,693 | 5,849 | 4,764 | 4,823 | 15,902 | 12,302 | 12,179 |
| 50,333 | 9,760 | 12,073 | 11,360 | 27,740 | 15,376 | 14,129 | 13,918 |
| 40,184 | 9,098 | 9,583 | 7,713 | 13,790 | 15,705 | 11,075 | 10,879 |
| 65,544 | 13,060 | 17,676 | 11,008 | 23,800 | 22,233 | 15,280 | 15,027 |

SEQUENCE LISTING

<160> NUMBER OF SEQ ID NOS: 40

<210> SEQ ID NO 1
<211> LENGTH: 22
<212> TYPE: DNA
<213> ORGANISM: Artificial Sequence.
<220> FEATURE:
<223> OTHER INFORMATION: Synthetic nucleic acid.

<400> SEQUENCE: 1
gtagcaggtg ccagctgtgt cg                                                22

<210> SEQ ID NO 2
<211> LENGTH: 25
<212> TYPE: DNA
<213> ORGANISM: Artificial Sequence.
<220> FEATURE:
<223> OTHER INFORMATION: Synthetic nucleic acid.

<400> SEQUENCE: 2
tttcatgggg ccatggtctg ttaca                                             25

<210> SEQ ID NO 3
<211> LENGTH: 23
<212> TYPE: DNA
<213> ORGANISM: Artificial Sequence.
<220> FEATURE:
<223> OTHER INFORMATION: Synthetic nucleic acid.

<400> SEQUENCE: 3
ccggccgtgg cactcattta ccc                                               23

<210> SEQ ID NO 4
<211> LENGTH: 25
<212> TYPE: DNA
<213> ORGANISM: Artificial Sequence.
<220> FEATURE:
<223> OTHER INFORMATION: Synthetic nucleic acid.

<400> SEQUENCE: 4
ggaggcagga gtacgtcatt taccg                                             25

<210> SEQ ID NO 5
<211> LENGTH: 22
<212> TYPE: DNA
<213> ORGANISM: Artificial Sequence.
<220> FEATURE:
<223> OTHER INFORMATION: Synthetic nucleic acid.

<400> SEQUENCE: 5
gtagcaggtg ccgtccrcct cc                                                22

<210> SEQ ID NO 6
<211> LENGTH: 66
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(34)
<223> OTHER INFORMATION: N can be any nucleotide.
<220> FEATURE:
<221> NAME/KEY: misc_feature
<222> LOCATION: (37)..(40)
<223> OTHER INFORMATION: N can be any nucleotide.
<220> FEATURE:
<221> NAME/KEY: misc_feature
<222> LOCATION: (43)..(47)
<223> OTHER INFORMATION: N can be any nucleotide.

<400> SEQUENCE: 6
gtgggctcgg agatgtgtat aagagacagn nnnnttnnnn ttnnnnnggg aagtagtcct    60
tgacca    66

<210> SEQ ID NO 7
<211> LENGTH: 65
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(36)
<223> OTHER INFORMATION: N can be any nucleotide.
<220> FEATURE:
<221> NAME/KEY: misc_feature
<222> LOCATION: (39)..(42)
<223> OTHER INFORMATION: N can be any nucleotide.
<220> FEATURE:
<221> NAME/KEY: misc_feature
<222> LOCATION: (45)..(47)
<223> OTHER INFORMATION: N can be any nucleotide.

<400> SEQUENCE: 7
gtgggctcgg agatgtgtat aagagacagn nnnnnttnn nnttnnnggg gaagaagccc    60
tggac    65

<210> SEQ ID NO 8
<211> LENGTH: 65
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(34)
<223> OTHER INFORMATION: N can be any nucleotide.
<220> FEATURE:
<221> NAME/KEY: misc_feature
<222> LOCATION: (37)..(40)
<223> OTHER INFORMATION: N can be any nucleotide.
<220> FEATURE:
<221> NAME/KEY: misc_feature
<222> LOCATION: (43)..(47)
<223> OTHER INFORMATION: N can be any nucleotide.

<400> SEQUENCE: 8
gtgggctcgg agatgtgtat aagagacagn nnnttnnnn ttnnnnnaag tagcccgtgg    60
ccagg    65

<210> SEQ ID NO 9
<211> LENGTH: 68
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(34)
<223> OTHER INFORMATION: N can be any nucleotide.
<220> FEATURE:
<221> NAME/KEY: misc_feature
<222> LOCATION: (37)..(40)
<223> OTHER INFORMATION: N can be any nucleotide.
<220> FEATURE:
<221> NAME/KEY: misc_feature
<222> LOCATION: (43)..(47)

<223> OTHER INFORMATION: N can be any nucleotide.

<400> SEQUENCE: 9
gtgggctcgg agatgtgtat aagagacagn nnnnttnnnn ttnnnnntgg gtggtaccca    60
gttatcaa    68

<210> SEQ ID NO 10
<211> LENGTH: 66
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(37)
<223> OTHER INFORMATION: N can be any nucleotide.
<220> FEATURE:
<221> NAME/KEY: misc_feature
<222> LOCATION: (40)..(43)
<223> OTHER INFORMATION: N can be any nucleotide.
<220> FEATURE:
<221> NAME/KEY: misc_feature
<222> LOCATION: (46)..(47)
<223> OTHER INFORMATION: N can be any nucleotide.

<400> SEQUENCE: 10
gtgggctcgg agatgtgtat aagagacagn nnnnnnnttn nnnttnngaa ggaagtcctg    60
tgcgag    66

<210> SEQ ID NO 11
<211> LENGTH: 70
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(32)
<223> OTHER INFORMATION: N can be any nucleotide.
<220> FEATURE:
<221> NAME/KEY: misc_feature
<222> LOCATION: (34)..(41)
<223> OTHER INFORMATION: N can be any nucleotide.
<220> FEATURE:
<221> NAME/KEY: misc_feature
<222> LOCATION: (43)..(49)
<223> OTHER INFORMATION: N can be any nucleotide.

<400> SEQUENCE: 11
gtcggcagcg tcagatgtgt ataagagaca gntnnnnnnn ntnnnnnnna tggactggac    60 ctggaggdtc    70

<210> SEQ ID NO 12
<211> LENGTH: 69
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(33)
<223> OTHER INFORMATION: N can be any nucleotide.
<220> FEATURE:
<221> NAME/KEY: misc_feature
<222> LOCATION: (35)..(42)
<223> OTHER INFORMATION: N can be any nucleotide.
<220> FEATURE:
<221> NAME/KEY: misc_feature
<222> LOCATION: (44)..(49)
<223> OTHER INFORMATION: N can be any nucleotide.

<400> SEQUENCE: 12
gtcggcagcg tcagatgtgt ataagagaca gnntnnnnnn nntnnnnnna tggctggayt    60
tggaggatc    69

<210> SEQ ID NO 13
<211> LENGTH: 71
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(34)
<223> OTHER INFORMATION: N can be any nucleotide.
<220> FEATURE:
<221> NAME/KEY: misc_feature
<222> LOCATION: (36)..(43)
<223> OTHER INFORMATION: N can be any nucleotide.
<220> FEATURE:
<221> NAME/KEY: misc_feature
<222> LOCATION: (45)..(49)
<223> OTHER INFORMATION: N can be any nucleotide.

<400> SEQUENCE: 13
gtcggcagcg tcagatgtgt ataagagaca gnnntnnnnn nnntnnnnna tggacacact    60
ttgttccacg c    71

<210> SEQ ID NO 14
<211> LENGTH: 71
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(35)
<223> OTHER INFORMATION: N can be any nucleotide.
<220> FEATURE:
<221> NAME/KEY: misc_feature
<222> LOCATION: (37)..(44)
<223> OTHER INFORMATION: N can be any nucleotide.
<220> FEATURE:
<221> NAME/KEY: misc_feature
<222> LOCATION: (46)..(49)
<223> OTHER INFORMATION: N can be any nucleotide.

<400> SEQUENCE: 14
gtcggcagcg tcagatgtgt ataagagaca gnnnntnnnn nnnntnnnna tggacacytt    60
tgctmcacac t    71

<210> SEQ ID NO 15
<211> LENGTH: 69
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(36)
<223> OTHER INFORMATION: N can be any nucleotide.
<220> FEATURE:
<221> NAME/KEY: misc_feature
<222> LOCATION: (38)..(45)
<223> OTHER INFORMATION: N can be any nucleotide.
<220> FEATURE:
<221> NAME/KEY: misc_feature
<222> LOCATION: (47)..(49)
<223> OTHER INFORMATION: N can be any nucleotide.

```
<400> SEQUENCE: 15
gtcggcagcg tcagatgtgt ataagagaca gnnnnntnnn nnnnntnnna tggagttkgg      60
gctgagctg                                                              69

<210> SEQ ID NO 16
<211> LENGTH: 69
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(37)
<223> OTHER INFORMATION: N can be any nucleotide.
<220> FEATURE:
<221> NAME/KEY: misc_feature
<222> LOCATION: (39)..(46)
<223> OTHER INFORMATION: N can be any nucleotide.
<220> FEATURE:
<221> NAME/KEY: misc_feature
<222> LOCATION: (48)..(49)
<223> OTHER INFORMATION: N can be any nucleotide.

<400> SEQUENCE: 16
gtcggcagcg tcagatgtgt ataagagaca gnnnnnntnn nnnnnntnna tgsatttgks      60
ctgagctgg                                                              69

<210> SEQ ID NO 17
<211> LENGTH: 69
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(38)
<223> OTHER INFORMATION: N can be any nucleotide.
<220> FEATURE:
<221> NAME/KEY: misc_feature
<222> LOCATION: (40)..(47)
<223> OTHER INFORMATION: N can be any nucleotide.
<220> FEATURE:
<221> NAME/KEY: misc_feature
<222> LOCATION: (49)..(49)
<223> OTHER INFORMATION: N can be any nucleotide.

<400> SEQUENCE: 17
gtcggcagcg tcagatgtgt ataagagaca gnnnnnnntn nnnnnnntna tgacggagtt      60
tgggctgag                                                              69

<210> SEQ ID NO 18
<211> LENGTH: 67
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(32)
<223> OTHER INFORMATION: N can be any nucleotide.
<220> FEATURE:
<221> NAME/KEY: misc_feature
<222> LOCATION: (34)..(40)
<223> OTHER INFORMATION: N can be any nucleotide.
<220> FEATURE:
<221> NAME/KEY: misc_feature
<222> LOCATION: (42)..(49)
<223> OTHER INFORMATION: N can be any nucleotide.

<400> SEQUENCE: 18
```

-continued gtcggcagcg tcagatgtgt ataagagaca gntnnnnnnn tnnnnnnnna tggaactggg    60
gctccgc                                                              67

<210> SEQ ID NO 19
<211> LENGTH: 73
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(33)
<223> OTHER INFORMATION: N can be any nucleotide.
<220> FEATURE:
<221> NAME/KEY: misc_feature
<222> LOCATION: (35)..(41)
<223> OTHER INFORMATION: N can be any nucleotide.
<220> FEATURE:
<221> NAME/KEY: misc_feature
<222> LOCATION: (43)..(49)
<223> OTHER INFORMATION: N can be any nucleotide.

<400> SEQUENCE: 19
gtcggcagcg tcagatgtgt ataagagaca gnntnnnnnn ntnnnnnnna tgaaacacct    60
gtggttcttc ctc                                                       73

<210> SEQ ID NO 20
<211> LENGTH: 68
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(34)
<223> OTHER INFORMATION: N can be any nucleotide.
<220> FEATURE:
<221> NAME/KEY: misc_feature
<222> LOCATION: (36)..(42)
<223> OTHER INFORMATION: N can be any nucleotide.
<220> FEATURE:
<221> NAME/KEY: misc_feature
<222> LOCATION: (44)..(49)
<223> OTHER INFORMATION: N can be any nucleotide.

<400> SEQUENCE: 20
gtcggcagcg tcagatgtgt ataagagaca gnnntnnnnn nntnnnnnna tgcaagtggg    60
ggcctctc                                                             68

<210> SEQ ID NO 21
<211> LENGTH: 68
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(35)
<223> OTHER INFORMATION: N can be any nucleotide.
<220> FEATURE:
<221> NAME/KEY: misc_feature
<222> LOCATION: (37)..(43)
<223> OTHER INFORMATION: N can be any nucleotide.
<220> FEATURE:
<221> NAME/KEY: misc_feature
<222> LOCATION: (45)..(49)
<223> OTHER INFORMATION: N can be any nucleotide.

<400> SEQUENCE: 21

```
gtcggcagcg tcagatgtgt ataagagaca gnnnntnnnn nnntnnnnna tggggtcaac    60
cgccatcc                                                             68
```

<210> SEQ ID NO 22
<211> LENGTH: 71
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(36)
<223> OTHER INFORMATION: N can be any nucleotide.
<220> FEATURE:
<221> NAME/KEY: misc_feature
<222> LOCATION: (38)..(44)
<223> OTHER INFORMATION: N can be any nucleotide.
<220> FEATURE:
<221> NAME/KEY: misc_feature
<222> LOCATION: (46)..(49)
<223> OTHER INFORMATION: N can be any nucleotide.

<400> SEQUENCE: 22

```
gtcggcagcg tcagatgtgt ataagagaca gnnnnntnnn nnnntnnnna tgtctgtctc    60
cttcctcatc t                                                         71
```

<210> SEQ ID NO 23
<211> LENGTH: 59
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(32)
<223> OTHER INFORMATION: N can be any nucleotide.
<220> FEATURE:
<221> NAME/KEY: misc_feature
<222> LOCATION: (35)..(41)
<223> OTHER INFORMATION: N can be any nucleotide.

<400> SEQUENCE: 23

```
gtgggctcgg agatgtgtat aagagacagn nnttnnnnnn nggaacacat ccggagcct     59
```

<210> SEQ ID NO 24
<211> LENGTH: 60
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(35)
<223> OTHER INFORMATION: N can be any nucleotide.
<220> FEATURE:
<221> NAME/KEY: misc_feature
<222> LOCATION: (38)..(41)
<223> OTHER INFORMATION: N can be any nucleotide.

<400> SEQUENCE: 24

```
gtgggctcgg agatgtgtat aagagacagn nnnnttnnnn ngaaaagggt tggggcggat    60
```

<210> SEQ ID NO 25
<211> LENGTH: 58
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(32)
<223> OTHER INFORMATION: N can be any nucleotide.
<220> FEATURE:
<221> NAME/KEY: misc_feature
<222> LOCATION: (35)..(41)
<223> OTHER INFORMATION: N can be any nucleotide.

<400> SEQUENCE: 25
gtgggctcgg agatgtgtat aagagacagn nnttnnnnnn naagaccgat gggcccctt    58

<210> SEQ ID NO 26
<211> LENGTH: 59
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(34)
<223> OTHER INFORMATION: N can be any nucleotide.
<220> FEATURE:
<221> NAME/KEY: misc_feature
<222> LOCATION: (37)..(41)
<223> OTHER INFORMATION: N can be any nucleotide.

<400> SEQUENCE: 26
gtgggctcgg agatgtgtat aagagacagn nnnnttnnnn ngaagacctt ggggctggt    59

<210> SEQ ID NO 27
<211> LENGTH: 60
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (30)..(32)
<223> OTHER INFORMATION: N can be any nucleotide.
<220> FEATURE:
<221> NAME/KEY: misc_feature
<222> LOCATION: (35)..(41)
<223> OTHER INFORMATION: N can be any nucleotide.

<400> SEQUENCE: 27
gtgggctcgg agatgtgtat aagagacagn nnttnnnnnn ngaagacgga tgggctctgt   60

<210> SEQ ID NO 28
<211> LENGTH: 67
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(32)
<223> OTHER INFORMATION: N can be any nucleotide.
<220> FEATURE:
<221> NAME/KEY: misc_feature
<222> LOCATION: (34)..(41)
<223> OTHER INFORMATION: N can be any nucleotide.
<220> FEATURE:
<221> NAME/KEY: misc_feature
<222> LOCATION: (43)..(49)
<223> OTHER INFORMATION: N can be any nucleotide.

<400> SEQUENCE: 28
gtcggcagcg tcagatgtgt ataagagaca gntnnnnnnn ntnnnnnnns cagctggtgc   60
agtctgg                                                            67

<210> SEQ ID NO 29

```
<211> LENGTH: 68
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(33)
<223> OTHER INFORMATION: N can be any nucleotide.
<220> FEATURE:
<221> NAME/KEY: misc_feature
<222> LOCATION: (35)..(42)
<223> OTHER INFORMATION: N can be any nucleotide.
<220> FEATURE:
<221> NAME/KEY: misc_feature
<222> LOCATION: (44)..(49)
<223> OTHER INFORMATION: N can be any nucleotide.

<400> SEQUENCE: 29
gtcggcagcg tcagatgtgt ataagagaca gnntnnnnnn nntnnnnnng tgcagctggt      60
ggagtctg                                                              68

<210> SEQ ID NO 30
<211> LENGTH: 68
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(34)
<223> OTHER INFORMATION: N can be any nucleotide.
<220> FEATURE:
<221> NAME/KEY: misc_feature
<222> LOCATION: (36)..(43)
<223> OTHER INFORMATION: N can be any nucleotide.
<220> FEATURE:
<221> NAME/KEY: misc_feature
<222> LOCATION: (45)..(49)
<223> OTHER INFORMATION: N can be any nucleotide.

<400> SEQUENCE: 30
gtcggcagcg tcagatgtgt ataagagaca gnnntnnnnn nnntnnnnnt caccttgaag      60
gagtctgg                                                              68

<210> SEQ ID NO 31
<211> LENGTH: 66
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(35)
<223> OTHER INFORMATION: N can be any nucleotide.
<220> FEATURE:
<221> NAME/KEY: misc_feature
<222> LOCATION: (37)..(44)
<223> OTHER INFORMATION: N can be any nucleotide.
<220> FEATURE:
<221> NAME/KEY: misc_feature
<222> LOCATION: (46)..(49)
<223> OTHER INFORMATION: N can be any nucleotide.

<400> SEQUENCE: 31
gtcggcagcg tcagatgtgt ataagagaca gnnnntnnnn nnnntnnnnt gcagctgcag      60
gagtcg                                                                66

<210> SEQ ID NO 32
<211> LENGTH: 67
```

<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(36)
<223> OTHER INFORMATION: N can be any nucleotide.
<220> FEATURE:
<221> NAME/KEY: misc_feature
<222> LOCATION: (38)..(45)
<223> OTHER INFORMATION: N can be any nucleotide.
<220> FEATURE:
<221> NAME/KEY: misc_feature
<222> LOCATION: (47)..(49)
<223> OTHER INFORMATION: N can be any nucleotide.

<400> SEQUENCE: 32
gtcggcagcg tcagatgtgt ataagagaca gnnnnntnnn nnnnntnnng tgcagctaca    60
gcagtgg                                                              67

<210> SEQ ID NO 33
<211> LENGTH: 67
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (32)..(37)
<223> OTHER INFORMATION: N can be any nucleotide.
<220> FEATURE:
<221> NAME/KEY: misc_feature
<222> LOCATION: (39)..(46)
<223> OTHER INFORMATION: N can be any nucleotide.
<220> FEATURE:
<221> NAME/KEY: misc_feature
<222> LOCATION: (48)..(49)
<223> OTHER INFORMATION: N can be any nucleotide.

<400> SEQUENCE: 33
gtcggcagcg tcagatgtgt ataagagaca gnnnnnntnn nnnnnntnng tacagctgca    60
gcagtca                                                              67

<210> SEQ ID NO 34
<211> LENGTH: 19
<212> TYPE: DNA
<213> ORGANISM: Artificial Sequence.
<220> FEATURE:
<223> OTHER INFORMATION: Synthetic nucleic acid.
<220> FEATURE:
<221> NAME/KEY: misc_feature
<222> LOCATION: (1)..(1)
<223> OTHER INFORMATION: This nucleotide may be 5' phosphorylated.

<400> SEQUENCE: 34
ctgtctctta tacacatct                                                 19

<210> SEQ ID NO 35
<211> LENGTH: 33
<212> TYPE: DNA
<213> ORGANISM: Artificial Sequence.
<220> FEATURE:
<223> OTHER INFORMATION: Synthetic nucleic acid.

<400> SEQUENCE: 35
tcgtcggcag cgtcagatgt gtataagaga cag                                 33

<210> SEQ ID NO 36

```
<211> LENGTH: 34
<212> TYPE: DNA
<213> ORGANISM: Artificial Sequence.
<220> FEATURE:
<223> OTHER INFORMATION: Synthetic nucleic acid.

<400> SEQUENCE: 36
gtctcgtggg ctcggagatg tgtataagag acag                                34

<210> SEQ ID NO 37
<211> LENGTH: 29
<212> TYPE: DNA
<213> ORGANISM: Artificial Sequence.
<220> FEATURE:
<223> OTHER INFORMATION: Synthetic nucleic acid.

<400> SEQUENCE: 37
aatgatacgg cgaccaccga gatctacac                                      29

<210> SEQ ID NO 38
<211> LENGTH: 24
<212> TYPE: DNA
<213> ORGANISM: Artificial Sequence.
<220> FEATURE:
<223> OTHER INFORMATION: Synthetic nucleic acid.

<400> SEQUENCE: 38
caagcagaag acggcatacg agat                                           24

<210> SEQ ID NO 39
<211> LENGTH: 19
<212> TYPE: DNA
<213> ORGANISM: Artificial Sequence.
<220> FEATURE:
<223> OTHER INFORMATION: Synthetic nucleic acid.

<400> SEQUENCE: 39
tcgtcggcag cgtcagatg                                                 19

<210> SEQ ID NO 40
<211> LENGTH: 20
<212> TYPE: DNA
<213> ORGANISM: Artificial Sequence.
<220> FEATURE:
<223> OTHER INFORMATION: Synthetic nucleic acid.

<400> SEQUENCE: 40
gtgggctcgg agatgtgtat                                                20
```

METHODS OF PRODUCING NUCLEIC ACID LIBRARIES AND COMPOSITIONS AND KITS FOR PRACTICING SAME

CROSS-REFERENCE TO RELATED APPLICATIONS

This application claims the benefit of U.S. Provisional Patent Application No. 62/186,152, filed Jun. 29, 2015, which application is incorporated herein by reference in its entirety.

INTRODUCTION

Recent advances in DNA sequencing have revolutionized the field of genomics, making it possible for even single research groups to generate large amounts of sequence data very rapidly and at a substantially lower cost. These high-throughput sequencing technologies make deep transcriptome sequencing and transcript quantification, whole genome sequencing and resequencing available to many more researchers and projects. The selection of an appropriate sequencing platform for particular types of experiments is an important consideration, and requires a detailed understanding of the technologies available, including sources of error, error rate, as well as the speed and cost of sequencing. While sequencing costs have drastically decreased, the throughput and costs of library preparation are now a limiting factor.

An advancement in library preparation was the introduction of a hyperactive variant of the Tn5 transposase that mediates the fragmentation of double-stranded DNA and ligates synthetic oligonucleotides at both ends in a 5-min reaction. Wild-type Tn5 transposon is a composite transposon in which two near-identical insertion sequences (IS50L and IS50R) flank three antibiotic resistance genes. Each IS50 contains two inverted 19-bp end sequences (ESs), an outside end (OE) and an inside end (IE). Wild-type ESs, however, have a relatively low activity and have been replaced in vitro by hyperactive mosaic end (ME) sequences. A complex of the transposase with the 19-bp ME is thus all that is necessary for transposition to occur, provided that the intervening DNA is long enough to bring two of these sequences close together to form an active Tn5 transposase homodimer. Transposition is a very infrequent event in vivo, and hyperactive mutants were historically derived by introducing three missense mutations in the 476 residues of the Tn5 protein (E54K, M56A, L372P), which is encoded by IS50R. Transposition works through a "cut-and-paste" mechanism, where the Tn5 excises itself from the donor DNA and inserts into a target sequence, creating a 9-bp duplication of the target. In current commercial solutions (Nextera® DNA kits, Illumina), free synthetic ME adaptors are end-joined to the 5'-end of the target DNA by the transposase.

SUMMARY

Aspects of the present disclosure include methods of producing nucleic acid libraries. In certain aspects, the methods include combining primers and template nucleic acid strands under conditions in which the primers are extended to produce primer extension products, and tagging the ends of the primer extension products to produce tagged extension products. The tagging includes adding a first sequencing adapter to a first end of the primer extension products, and adding a second sequencing adapter to a second end of the primer extension products opposite the first end, where the nucleic acid sequences of the first and second sequencing adapters are different. According to certain embodiments, the methods further include: contacting a first aliquot of the tagged extension products with a first transposome including a transposon that includes all or a portion of the second sequencing adapter, to produce tagged extension product fragments including the first end and a shortened end including all or a portion of the second sequencing adapter; and contacting a second aliquot of the tagged extension products with a second transposome including a transposon that includes all or a portion of the first sequencing adapter, to produce tagged extension product fragments including the second end and a shortened end including all or a portion of the first sequencing adapter. Also provided are compositions and kits that find use, e.g., in practicing embodiments of the methods.

BRIEF DESCRIPTION OF THE FIGURE

FIG. 3 depicts the numbers of sequencing reads and molecules at different stages of analysis according to an embodiment of the present disclosure.

DETAILED DESCRIPTION

Figure 1:
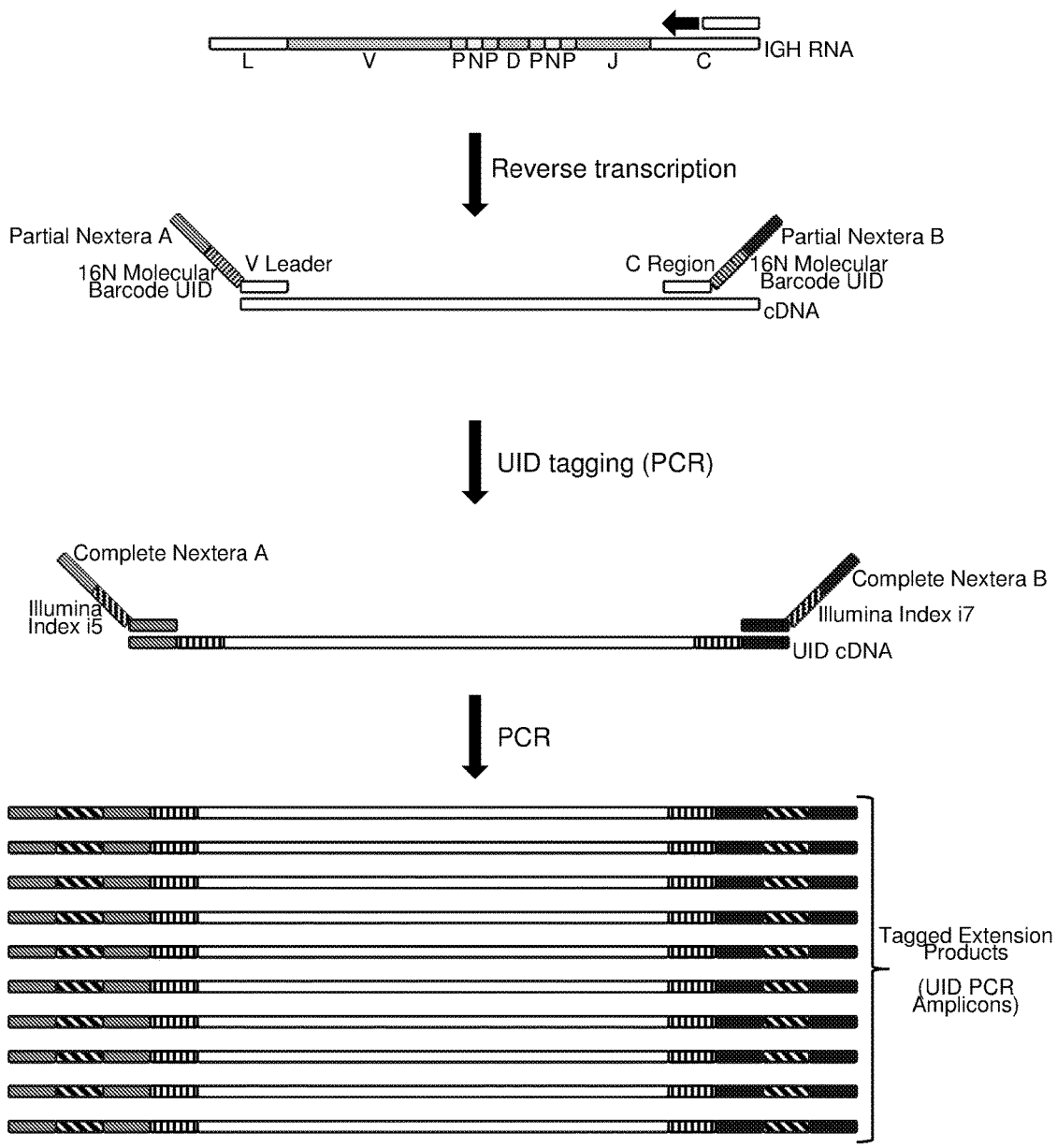
FIGS. 1A-1G schematically illustrate a method according to one embodiment of the present disclosure.
Figure 1:
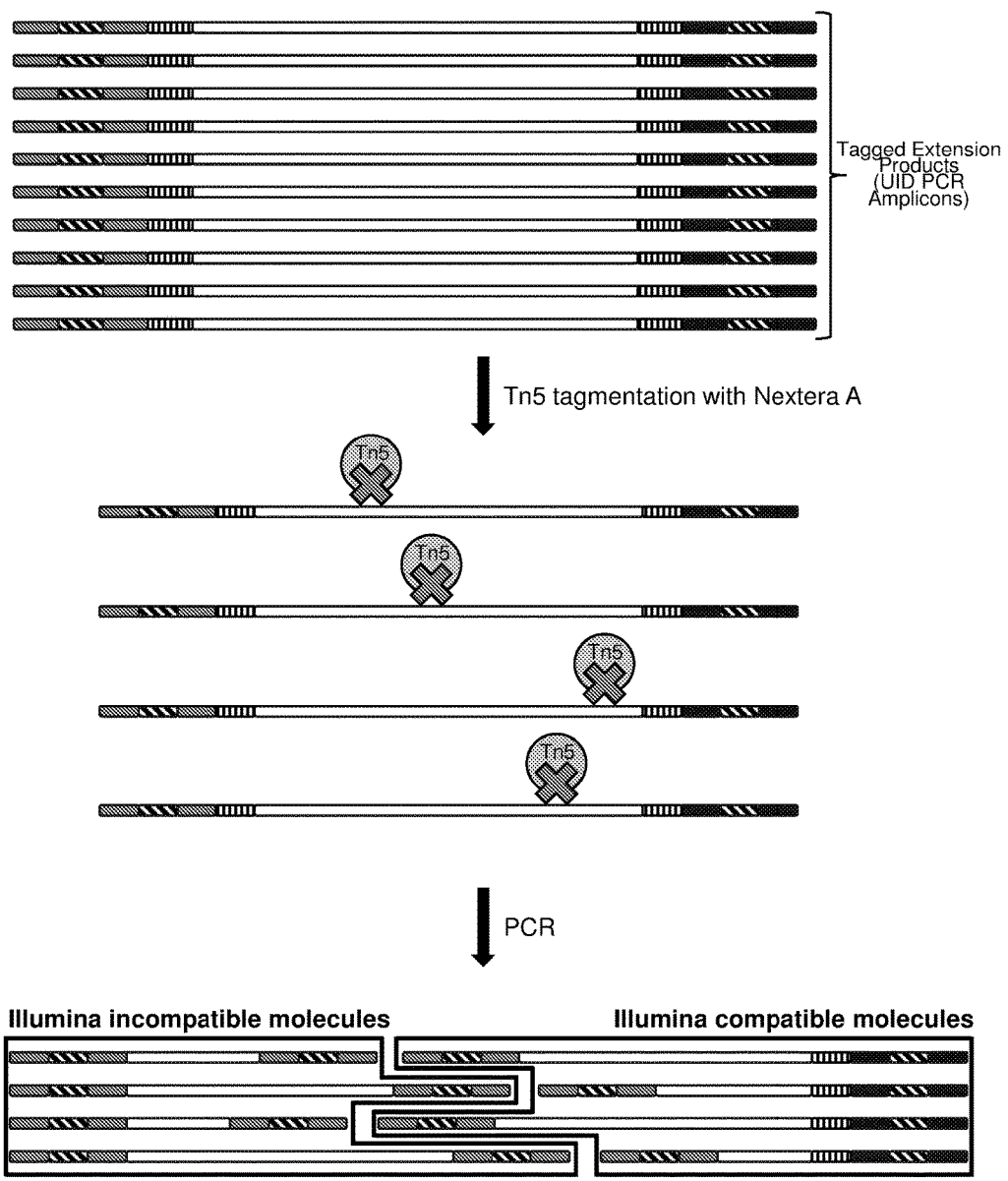
Figure 1:
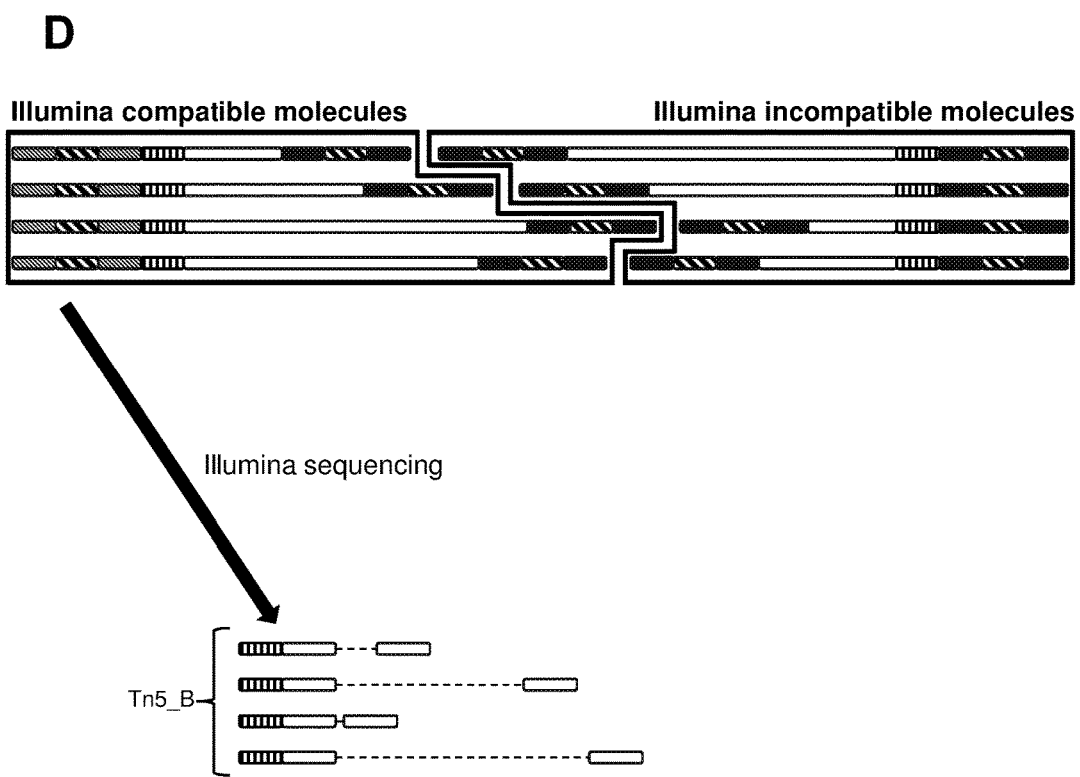
Figure 1:
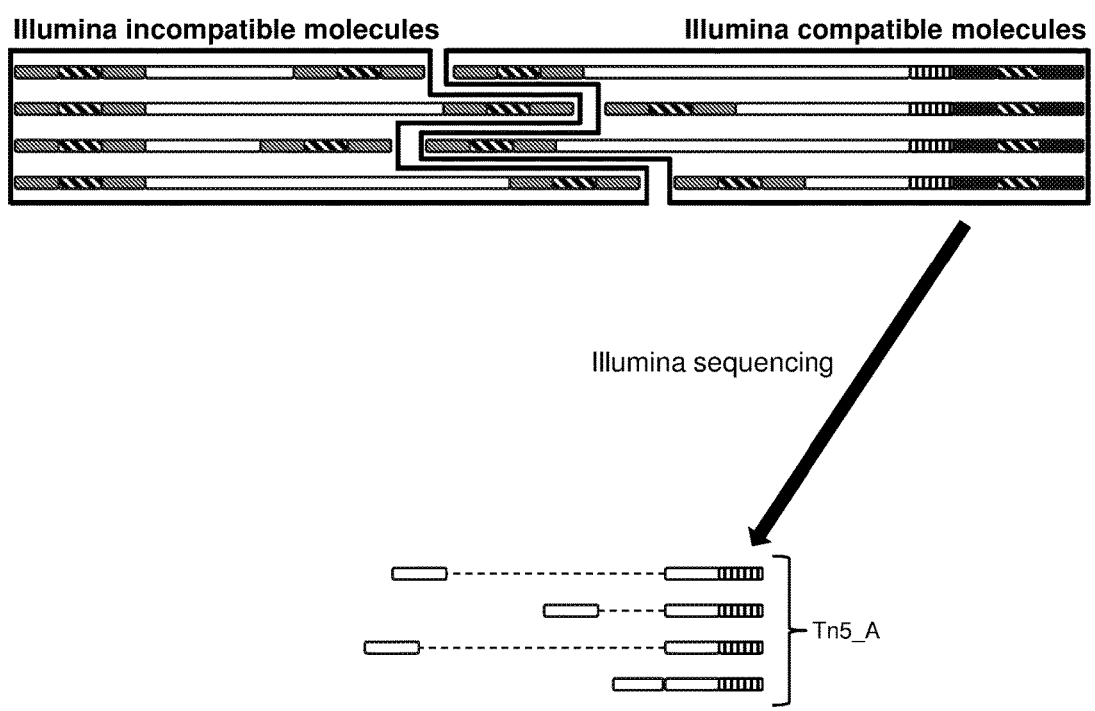
Figure 1:
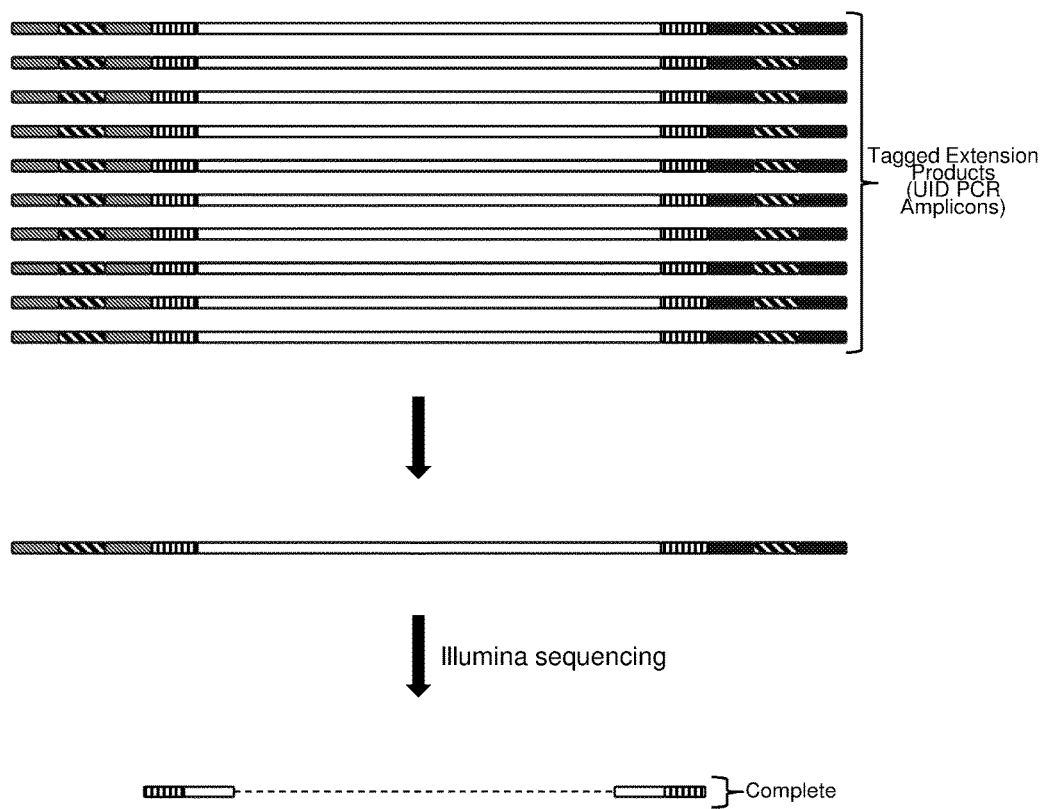

Aspects of the present disclosure include methods of producing nucleic acid libraries. In certain aspects, the methods include producing tagged primer extension products, and contacting aliquots of the tagged primer extension products with transposomes to produce tagged extension product fragments. The methods may further include sequencing the tagged primer extension products and/or tagged extension product fragments to determine the sequences of nucleic acids of interest. Also provided are compositions and kits that find use, e.g., in practicing embodiments of the methods.

Before the methods, compositions, and kits of the present disclosure are described in greater detail, it is to be understood that the methods, compositions, and kits are not limited to particular embodiments described, as such may, of course, vary. It is also to be understood that the terminology used herein is for the purpose of describing particular embodiments only, and is not intended to be limiting, since the scope of the methods, compositions, and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions, and kits. The upper and lower limits of these smaller ranges may independently be included in the smaller ranges and are also encompassed within the methods, compositions, and kits, subject to any specifically excluded limit in the stated range. Where the stated range includes one or both of the limits, ranges excluding either or both of those included limits are also included in the methods, compositions, and kits.

Unless defined otherwise, all technical and scientific terms used herein have the same meaning as commonly understood by one of ordinary skill in the art to which the methods, compositions, and kits belong. Although any methods, compositions, and kits similar or equivalent to those described herein can also be used in the practice or testing of the methods, compositions, and kits, representative illustrative methods, compositions, and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions, and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions, and kits, which are, for clarity, described in the context of separate embodiments, may also be provided in combination in a single embodiment. Conversely, various features of the methods, compositions, and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions/kits. In addition, all sub-combinations listed in the embodiments describing such variables are also specifically embraced by the present methods, compositions, and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, compositions, and kits. Any recited method can be carried out in the order of events recited or in any other order that is logically possible.

Methods

As summarized above, aspects of the present disclosure include methods of producing nucleic acid libraries.

The methods include combining primers and template nucleic acid strands under conditions in which the primers are extended to produce primer extension products. By "conditions in which the primers are extended to produce primer extension products" is meant reaction conditions that permit polymerase-mediated extension of a 3' end of a primer hybridized to the template nucleic acid strand. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner. For example, in addition to template nucleic acid strands, primers, a polymerase, and dNTPs, the reaction mixture may include buffer components that establish an appropriate pH, salt concentration, metal cofactor concentration (e.g., $Mg^{2+}$ or $Mn^{2+}$ concentration), and the like, for the extension reaction to occur. Other components may be included, such as one or more nuclease inhibitors (e.g., an RNase inhibitor and/or a DNase inhibitor), one or more additives for facilitating amplification/replication of GC rich sequences, betaine, single-stranded binding proteins (e.g., T4 Gene 32, cold shock protein A (CspA), and/or the like), DMSO, ethylene glycol, 1,2-propanediol, one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions. In certain aspects, when the template nucleic acid strand is an RNA, and when the extension reaction has proceeded for a desired amount of time, RNase H is added to hydrolyze any template RNAs that hybridized to the nascent cDNA strands.

The reaction mixture can have a pH suitable for the primer extension reaction. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production primer extension may vary according to factors such as the particular polymerase employed, the melting temperatures of the template nucleic acid strands and primers employed, etc. According to one embodiment, the polymerase is a reverse transcriptase (e.g., an MMLV reverse transcriptase) and the reaction mixture conditions sufficient to produce the extension products include bringing the reaction mixture to a temperature ranging from 4° C. to 72° C., such as from 16° C. to 70° C., e.g., 37° C. to 50° C., such as 40° C. to 45° C., including 42° C. In certain aspects, the polymerase is a thermostable polymerase (e.g., a Taq polymerase) and the conditions sufficient to produce the extension products include bringing the reaction mixture to an extension temperature ranging from 60° C. to 80° C., such as from 65° C. to 75° C., e.g., 68° C. to 72° C.

As summarized above, the methods include tagging the ends of the primer extension products to produce tagged extension products. The tagging includes adding a first sequencing adapter to a first end of the primer extension products, and adding a second sequencing adapter to a second end of the primer extension products opposite the first end, where the nucleic acid sequences of the first and second sequencing adapters are different. By "sequencing adapter" is meant one or more nucleic acid domains that include at least a portion of a nucleic acid sequence (or complement thereof) utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the sequencing adapter is, or includes, a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest, e.g., to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

The first and second sequencing adapters may be added using any convenient approach. According to certain embodiments, the adapters are ligated to the ends of the template nucleic acids. In other aspects, tagging the ends of the primer extension products includes amplifying the primer extension products using an amplification primer pair. The amplification primer pair includes a first amplification primer that includes a 3' hybridization region and a 5' region including all or a portion of the first sequencing adapter, and a second amplification primer that includes a 3' hybridization region and a 5' region comprising all or a portion of the second sequencing adapter.

When the first and second amplification primers include only a portion of the first and second sequencing adapters, respectively, tagging the ends of the primer extension products may further include amplifying the amplicons generated using the first and second primers with a second amplification primer pair. The second amplification primer pair includes a third amplification primer that includes a 3' hybridization region and a 5' region including the remaining portion of the first sequencing adapter, and a fourth amplification primer that includes a 3' hybridization region and a 5' region including the remaining portion of the second sequencing adapter.

The primers used to produce the primer extension reaction products, as well as any amplification primers employed, may be designed to be sufficiently complementary to the template nucleic acid strands or amplicons thereof such that the primers specifically hybridize to a region of the nucleic acid template under hybridization conditions.

The term "complementary" as used herein refers to a nucleotide sequence that base-pairs by non-covalent bonds to a region of the template nucleic acid strand or an amplicon thereof. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, the primers may be perfectly (i.e., 100%) complementary to the template nucleic acid strand or an amplicon thereof, or the primer may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As used herein, the term "hybridization conditions" means conditions in which a primer specifically hybridizes to a region of template nucleic acid strand or an amplicon thereof. Whether a primer specifically hybridizes to a template nucleic acid is determined by such factors as the degree of complementarity between the primer and the target nucleic acid and the temperature at which the hybridization occurs, which may be informed by the melting temperature ($T_M$) of the primer. The melting temperature refers to the temperature at which half of the primer-template nucleic acid duplexes remain hybridized and half of the duplexes dissociate into single strands. The $T_m$ of a duplex may be experimentally determined or predicted using the following formula $T_m = 81.5 + 16.6(\log_{10} [Na^+]) + 0.41$ (fraction G+C)−(60/N), where N is the chain length and $[Na^+]$ is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict $T_m$ of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The 3' hybridization regions of the amplification primers may be random or non-random. A non-random "pool" (or "panel") of two or more first-strand synthesis and/or amplification primers may be employed. Such pools find use, e.g., when multiplexed amplification of multiple nucleic acids or nucleic acid regions of interest is desirable, e.g., for transcriptome and/or exome sequencing, targeted sequencing, SNP genotyping/variant detection by sequencing, aneuploidy analysis, genomic profiling, expression profiling, and/or the like. Such primer pools may be specifically designed by one practicing the subject methods, or the practitioner may order one of the various commercially available primer pools, such as an Ion AmpliSeq™ Cancer Hotspot Panel available from Life Technologies, Inc. (Carlsbad, Calif.).

The methods of producing sequencing libraries according to the present disclosure include contacting a first aliquot of the tagged extension products with a first transposome including a transposon that includes all or a portion of the second sequencing adapter, to produce tagged extension product fragments including the first end and a shortened end including all or a portion of the second sequencing adapter. The methods also include contacting a second aliquot of the tagged extension products with a second transposome including a transposon that includes all or a portion of the first sequencing adapter, to produce tagged extension product fragments including the second end and a shortened end including all or a portion of the first sequencing adapter.

As used herein, a "transposome" is a complex of a transposase and a transposon. The transposase may be any suitable transposase, such as a Tn5 transposase, a Tn7 transposase, a Mu transposase, or the like. The transposon includes a sequencing adapter flanked by recognition sequences for the transposase being employed. For example, when the transposome includes a Tn5 transposase, the transposon includes the sequencing adapter flanked by Tn5 transposase recognition sequences (e.g., 19 base pair mosaic end (ME) sequences).

Upon contacting the first and second aliquots with the first and second transposomes, the transposons of the transposomes are inserted randomly into the tagged extension products. The result is the production of a group of tagged extension product fragments, each tagged extension product fragment of the group including an original end (and corresponding original sequencing adapter), and a shortened end that includes the sequencing adapter present in the transposon. In this group, the sequencing adapter provided by the transposome is different from the sequencing adapter at the original end of the tagged extension product. Having different sequencing adapters at the ends of the fragments finds use, e.g., when it is desirable to sequence the nucleic acid flanked by the adapters using a sequencing platform that requires different adapters at each end (e.g., an Illumina sequencing system or other such sequencing system).

The aliquots are contacted with the transposomes under conditions suitable for insertion of the transposon into the tagged extension products. Such conditions may vary depending upon the particular transposase employed. Typically, the conditions will include incubating the transposomes and tagged extension products in a buffered reaction mixture (e.g., a reaction mixture buffered with Tris-acetate, or the like) at a pH of from 7 to 8, such as pH 7.5. The transposome may be provided such that about a molar equivalent, or a molar excess, of the transposon is present relative to the tagged extension products. Suitable temperatures include from 32 to 42° C., such as 37° C. The reaction is allowed to proceed for a sufficient amount of time, such as from 10 minutes to 3 hours. The reaction may be terminated by adding a solution (e.g., a "stop" solution), which may include an amount of SDS and/or other transposase reaction termination reagent suitable to terminate the reaction. Protocols and materials for achieving fragmentation of nucleic acids using transposomes are available and include, e.g., those provided in the EZ-Tn5™ transpose kits available from Epicentre®.

According to certain embodiments, the methods of the present disclosure further include sequencing the tagged extension product fragments of the first aliquot, the tagged extension product fragments of the second aliquot, and an aliquot of unfragmented (or "complete") tagged extension products. The sequencing may be carried out on any suitable sequencing platform, including a Sanger sequencing platform, a next generation sequencing (NGS) platform (e.g., using a next generation sequencing protocol), or the like. NGS sequencing platforms of interest include, but are not limited to, a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Detailed protocols for preparing the tagged extension products and/or fragments thereof for sequencing (e.g., by further amplification (e.g., solid-phase amplification), or the like), sequencing the amplicons, and analyzing the sequencing data are available from the manufacturer of the sequencing system of interest.

When the methods include sequencing the tagged extension product fragments and the tagged extension products, the methods may further include assembling sequencing reads produced during the sequencing to determine sequences of interest of the template nucleic acids strands. For example, the inventors have developed a three-step assembly process suitable for assembling the sequencing reads produced according to embodiments of the present methods. First, a program identifies which reads are derived from a given amplicon (e.g., based on barcodes present in the sequencing adapters) and sorts those reads into three categories: those derived from the 5' "end"; those derived from the 3' "end"; and those that are unanchored and likely derived from a central region of the amplicon. Second, the program creates a high-quality consensus of the ends of the amplicon using a combination of quality and abundance of each nucleotide at each position. Third, the program reduces all of the reads into kmers and extends one of the ends until the program reaches the other end of the amplicon, or the program runs out of extensions. Finally, the program may report the completed amplicon in fastq format. When multiple extensions are possible, the program selects the extension which results in the highest-quality base being incorporated into the extension.

A method according to one embodiment of the present disclosure is schematically illustrated in FIGS. 1A-1G. In this example, as shown in FIG. 1A, the template nucleic acid strand is an immunoglobulin heaving chain (IgH) transcript, the primer extension reaction is a reverse transcription reaction, and the extension product is a cDNA. According to this embodiment, the extension product is tagged by successive PCR amplifications. The first amplification (designated "UID tagging" in FIG. 1A) employs a first primer that includes a 3' hybridization region that hybridizes to a V leader sequence of the cDNA, and a 5' region that includes a partial sequencing adapter that includes a 16N molecular barcode unique identifier (UID) and a partial Nextera A sequence. The second primer for the first amplification includes a 3' hybridization region that hybridizes to a C region of the cDNA, and a 5' region that includes a 16N molecular barcode unique identifier (UID) and a partial Nextera B sequence.

The second amplification (designated "PCR" in FIG. 1A) employs a third primer that includes a 3' hybridization region that hybridizes to the partial Nextera A sequence of amplicons generated in the first round of amplification, and a 5' region that includes an Illumina Index i5 sequence and the remainder of the Nextera A sequence, thereby completing the Nextera A component of the sequencing adapter. The second amplification employs a fourth primer that includes a 3' hybridization region that hybridizes to the partial Nextera B sequence of amplicons generated in the first round of amplification, and a 5' region that includes an Illumina Index i7 sequence and the remainder of the Nextera B sequence, thereby completing the Nextera B component of the sequencing adapter.

The result of the second amplification is the production of tagged extension products, which in the example shown in FIG. 1 are tagged amplicons corresponding to IgH transcript-derived cDNA used as template in the first round of amplification. The tagged amplicons include a first sequencing adapter having the 16N molecular barcode unique identifier (UID), the Illumina Index i5 sequence, and the complete Nextera A sequence. The tagged amplicons include a second sequencing adapter at the opposite end, the second sequencing adapter having the 16N molecular barcode unique identifier (UID), the Illumina Index i7 sequence, and the complete Nextera B sequence.

As shown in FIG. 1B, a first aliquot of the tagged extension products is contacted with a transposome that includes a Tn5 transposase and a transposon that includes the second sequencing adapter, thereby producing two groups of tagged extension product fragments. In a first group, shown on the left at the bottom of FIG. 1B, the fragments have the first sequencing adapter at one end (the original end) and the second sequencing adapter provided by the transposome at the other (shortened) end. Such fragments are compatible for sequencing on sequencing systems that require the first and second ends of molecules to be sequenced to have different adapters (e.g., an Illumina sequencing system). In the second group, shown on the right at the bottom of FIG. 1B, the fragments have the second sequencing adapter at one end (the original end) and the second sequencing adapter provided by the transposome at the other (shortened) end. Such fragments are incompatible for sequencing on sequencing systems that require the first and second ends of nucleic acids to be sequenced to have different adapters.

As shown in FIG. 1C, a second aliquot of the tagged extension products are contacted with a transposome that includes a Tn5 transposase and a transposon that includes the first sequencing adapter, thereby producing two groups of tagged extension product fragments. In a first group, shown on the right at the bottom of FIG. 1C, the fragments have the second sequencing adapter at one end (the original end) and the first sequencing adapter provided by the transposome at the other (shortened) end. In the second group, shown on the left at the bottom of FIG. 1C, the fragments have the first sequencing adapter at one end (the original end) and the first sequencing adapter provided by the transposome at the other (shortened) end.

At the bottom of FIGS. 1D and 1E are schematic illustrations of the sequence information obtained upon sequencing the tagged extension product fragments shown in FIGS. 1B and 1C, respectively, on a sequencer that requires different adapters at each end (e.g., an Illumina sequencing system). As shown in FIG. 1F, unfragmented ("complete") tagged extension products having the original ends/adapters are also sequenced according to this example. The sequence information obtained upon sequencing the "complete" tagged extension products is schematically illustrated at the bottom of FIG. 1F.

According to this example, the sequencing reads obtained from sequencing the tagged extension product fragments from the first and second aliquots, as well as the reads obtained from sequencing the complete (unfragmented) tagged extension products, are assembled and annotated, as schematically illustrated in FIG. 1G. Based on the template nucleic acid strand of this particular example, the method produces a complete annotated sequence of the original IgH RNA transcript schematically shown at the top of FIG. 1A.

Sequencing libraries of any nucleic acid(s) of interest may be prepared, and optionally sequenced, using the methods of the present disclosure. The template nucleic acid strands (e.g., template RNAs, template DNA strands, or the like) may be polymers of any length composed of deoxyribonucleotides, ribonucleotides, or combinations thereof, e.g., 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer or more bases. In certain aspects, the template nucleic acid strand is a polymer composed of deoxyribonucleotides or ribonucleotides, e.g., 10 bases or less, 20 bases or less, 50 bases or less, 100 bases or less, 500 bases or less, 1000 bases or less, 2000 bases or less, 3000 bases or less, 4000 bases or less, or 5000 bases or less.

According to certain embodiments, the template nucleic acid strands are template ribonucleic acids (template RNA). The template RNA may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

According to certain embodiments, the template nucleic acid strands are template mRNAs. The mRNAs may encode any proteins of interest (e.g., mRNAs isolated from any of the sources above). In certain aspects, the template nucleic acid strands are mRNAs that encodes immunoglobulins, such as an IgG, IgM, IgA, IgD and IgE. For example, the mRNAs may encode antibodies produced by B cells (e.g., memory B cells). Producing a sequencing library from such mRNAs finds use, e.g., in analyzing the differential response of the antibody repertoire to vaccinations (e.g., live-attenuated or trivalent-inactivated influenza vaccination, and the like). Details regarding such analyses may be found in Vollmers et al. (2013) PNAS 110(33):13463-13468.

The template nucleic acid strands may be tumor-specific genes and/or tumor-associated genes, or RNAs transcribed therefrom. Tumor-specific genes include genes that are expressed in malignant cells and not expressed in non-malignant cells. Tumor-associated genes are genes expressed in malignant cells with limited expression in cells of normal tissues, genes that are expressed at much higher levels in malignant versus normal cells, or genes that are developmentally expressed.

In certain aspects, the template nucleic acid strands are template deoxyribonucleic acid (DNA) strands. Template DNAs of interest include, but are not limited to, genomic DNA or fragments thereof, complementary DNA (or "cDNA", synthesized from any RNA or DNA of interest), recombinant DNA (e.g., plasmid DNA), or the like.

The template nucleic acid strands may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse or rat), or any other mammal of interest). In other aspects, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source.

According to certain embodiments, the nucleic acid sample is a tumor nucleic acid sample (that is, a nucleic acid sample isolated from a tumor). "Tumor", as used herein, refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like.

Approaches, reagents and kits for isolating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Md.); the DNAzol®, ChargeSwitch®, Purelink®, GeneCatcher® nucleic acid isolation/purification kits by Life Technologies, Inc. (Carlsbad, Calif.); the NucleoMag®, NucleoSpin®, and NucleoBond® nucleic acid isolation/purification kits by Clontech Laboratories, Inc. (Mountain View, Calif.). In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, Calif.), and the NucleoSpin® FFPE kits by Clontech Laboratories, Inc. (Mountain View, Calif.).

Compositions

Also provided are compositions. The compositions find use, e.g., in practicing the methods of the present disclosure, and may include any components (e.g., template nucleic acids, tagged extension products and/or fragments thereof, extension and/or amplification primers, transposomes, etc.) described hereinabove in the section describing the methods of the present disclosure, in any desired combination.

According to certain embodiments, a composition of the present disclosure includes a plurality of tagged extension products, each of the plurality of tagged extension products including a first sequencing adapter at a first end of a primer extension product, and a second sequencing adapter at a second end of the primer extension product. The nucleic acid sequences of the first and second sequencing adapters are different. Such compositions further include transposomes including transposons, each of the transposons including all or a portion of the first sequencing adapter, or all or a portion of the second sequencing adapter.

Any of the compositions of the present disclosure may be present in a container. Suitable containers include, but are not limited to, tubes, vials, and plates (e.g., a 96- or other-well plate).

Any of the compositions of the present disclosure may be present in a device. Devices of interest include, but are not limited to, an incubator, a thermocycler, a sequencing system (e.g., a Sanger sequencing system or a next generation sequencing system), a microfluidic device, or the like.

Kits

As summarize above, the present disclosure provides kits. The kits may include, e.g., any useful components (e.g., extension and/or amplification primers, transposomes or components thereof, reaction buffers, etc.) described hereinabove in the section describing the methods of the present disclosure, in any desired combination. In certain aspects, a kit of the present disclosure includes a first amplification primer that includes a 3' hybridization region and a 5' region including all or a portion of a first sequencing adapter. The kit further includes a second amplification primer that includes a 3' hybridization region and a 5' region including all or a portion of a second sequencing adapter. Also included in such kits is a transposase, a transposon including all or a portion of the first sequencing adapter, and a transposon including all or a portion of the second sequencing adapter.

Any other components or reagents useful in producing sequencing libraries according to the methods of the present disclosure may be provided in the subject kits. In certain aspects, the kits include one or more reaction buffers (e.g., in a concentrated form), cofactors, etc. for preparing a reaction mixture suitable for first strand synthesis, amplification, transposition, and the like.

Components of the kits may be present in separate containers, or multiple components may be present in a single container. For example, the transposon including all or a portion of the first sequencing adapter and the transposon including all or a portion of the second sequencing adapter may be provided in separate containers. The transposase may be "pre-loaded" with a transposon, such that the kits include pre-formed transposomes. A suitable container includes a single tube (e.g., vial), one or more wells of a plate (e.g., a 96-well plate, a 384-well plate, etc.), or the like.

The kits may include instructions, such as instructions for producing a library of nucleic acids, e.g., according to embodiments of the methods of the present disclosure. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Utility

The methods, compositions and kits of the present disclosure find use in a variety of applications, including any applications in which it is desirable to prepare nucleic acids for sequencing on a sequencing system. Applications of interest include, e.g., research applications and clinical applications (e.g., clinical diagnostic applications).

According to certain embodiments, the present methods, compositions, and kits find use in sequencing nucleic acids of interest that are too large to be sequenced on a short read sequencing system (e.g., a short read Illumina sequencing system). Compared to existing protocols for amplicon sub-assembly—which rely upon mechanical fragmentation, tiled primers, and the like—the present methods are more efficient and less complicated. Sequencing of amplicons of approximately 500 bp is possible using the Illumina MiSeq® sequencer and a 2×300 protocol, yet at low throughput and relatively high cost. Both throughput and cost are improved according to the methods of the present invention, which enables amplicons with, for example, lengths greater than 500 bp (e.g., 500 bp to 1000 bp, or 600 to 1000 bp) to be sequenced (e.g., on an Illumina sequencing system) using, e.g., 2×150 bp paired end sequencing. For example, methods of the present invention enables amplicons (e.g., tagged extension product amplicons) with lengths of from 400 to 1000 bp (e.g., from 450 to 800 bp) to be sequenced with high accuracy and throughput. In some embodiments, the methods of the present disclosure include sequencing (e.g., with high accuracy and throughput) amplicons (e.g., tagged extension product amplicons) of from 400 to 800 bp, 425 to 800 bp, 450 to 800 bp, 475 to 800 bp, 500 to 800 bp, 525 to 800 bp, 550 to 800 bp, 575 to 800 bp, 600 to 800 bp, 625 to 800 bp, 650 to 800 bp, 675 to 800 bp, 700 to 800 bp, 725 to 800 bp, 750 to 800 bp, or 775 to 800 bp in length.

The methods, compositions, and kits of the present disclosure find use in preparing sequencing libraries, and optionally determining the sequences of, any nucleic acids of interest (e.g., RNAs, DNAs, and any subtypes thereof). For example, the methods, compositions, and kits find use in preparing sequencing libraries, and optionally determining the sequences of, immunoglobulin heavy chain (IgH) transcripts for immune repertoire sequencing, e.g., for diagnostic, biomarker, and antibody production purposes. For example, the methods, compositions, and kits may find use in determining the sequences of immune repertoire amplicons that have been prepared using 5' RACE. The methods, compositions, and kits of the present disclosure may also find use in amplicon based applications outside of immune repertoire sequencing, for example, in sequencing of 16S RNA and cancer amplicon panels.

The following examples are offered by way of illustration and not by way of limitation.

Experimental

Antibody repertoire sequencing is a powerful tool to analyze the adaptive immune system. To sequence entire antibody repertoires, amplicons are created from antibody heavy chain (IGH) transcripts and sequenced on a high-throughput sequencer. A method is presented below that combines Tn5 transposase and molecular identifiers for the highly accurate sequencing of amplicons longer than 500 bp using Illumina short read paired end sequencing. This method is then applied to antibody heavy chain amplicons to sequence a highly accurate full-length immune repertoire. This method, designated Tn5 enabled Molecular Identifier guided Amplicon Sequencing (TMIseq), is based on a library preparation protocol utilizing molecular barcoding of individual molecules and Tn5 tagmentation enabling the sequencing of molecules exceeding Illumina read length.

Materials and Methods

PBMC Extraction and RNA Purification

Samples were processed by Ficoll-Gradient (GE-Health) to extract PBMCs. PBMC were lysed directly in RLT buffer and frozen at −80° C. until RNA was extracted. RNA was extracted from 400,000 cells each using the RNeasy Mini Kit (Qiagen). Resulting RNA concentrations ranged from 20-50 ng/ul.

TMIseq Library Preparation 10 ul of RNA was used for Superscript II (Thermo) cDNA first strand synthesis using a primer pool specific to all exons specific to the secreted isoform of all IGH isotypes (IgM, IgD, IgG1-4, IgA1-2, IgE). In a 2 cycle PCR reaction 2nd and 3rd cDNA strands were synthesized using Phusion polymerase (Thermo) and 2 modified primer pools complementary to the beginning of the V-Leader exons and about 100 bp into CH1 exons of all IGH isotypes and containing molecular identifiers and partial Nextera Sequences. cDNA was purified and size selected twice with SPRI beads using a 0.7:1 (Beads:Sample) ratio corresponding to a cutoff discarding DNA shorter than 300 bp. In a 30 cycle PCR reaction 3rd cDNA strands were amplified using a pair of primers containing complete Nextera sequences as well as Illumina i5 and i7 indexes to index each individual sample (Nextera_Primer_A and Nextera_Primer_B) Nextera_Primer_A represents a group of sequences each of which are made up of the Nextera_Primer_A_5 (SEQ ID NO:37) at the 5' end and Nextera_Primer_A_3 (SEQ ID NO:39) at the 3' end with an intervening i5 index sequence. Nextera_Primer_B represents a group of sequences each of which are made up of the Nextera_Primer_B_5 (SEQ ID NO:38) at the 5' end and Nextera_Primer_B_3 (SEQ ID NO:40) at the 3' end with an intervening i7 index sequence. Intervening i5 and i7 sequences are known by those of ordinary skill in the art and can be found in an Illumina Adapter Sequences Document obtained from "http:" followed by "//support.illumina." followed by "com/downloads/illumina-customer-sequence-letter." followed by "html", which is incorporated herein by reference. Samples with unique i5 and i7 indexes (i.e. each sample can be uniquely distinguished by either i5 or i7 index, e.g. Sample 1: i5_1, i7_1; Sample 2: i5_2, i7_2; etc. . . . ) are pooled and split into three aliquots. To create Tn5_A libraries, aliquot 1 is tagmented using Tn5 enzyme loaded with Nextera_A adapter and PCR amplified using a universal Nextera_B primer and a Nextera_A primer with a Illumina Index not yet present in the library pool and purified and size selected for fragments larger than 380 bp using 2% EX Gels (Life). To create Tn5_B libraries, aliquot 2 is tagmented using Tn5 enzyme loaded with Nextera_B adapter and PCR amplified using a universal Nextera_A primer and a Nextera_B primer with a Illumina Index not yet present in the library pool and purified and size selected for fragments larger than 380 bp using 2% EX Gels (Life). Uncut (aliquot 3), Tn5_A, and Tn5_B libraries were pooled and sequenced according to standard Illumina protocols on an Illumina MiSeq 2×300 run or HiSeq3000 2×150 run.

Control Library Preparation

Control libraries were generated as TMIseq libraries with the exceptions to the primer pools used for 2nd and 3rd strand cDNA synthesis. The FR1 specific primer pool was designed to bind 1-10 bp into the FR1 region (see, TABLE 1, SEQ ID NOs:28-33), while the C specific primer pool was designed to bind 20 bp into the CH1 exons of all IGH isotypes (see, TABLE 1, SEQ ID NOs:23-27). The resulting library with an insert size of ~400 bp is sequenced on an Illumina MiSeq 2×300 bp run.

Raw Data Processing Data Assembly

Raw reads in fastq format are trimmed using trimmomatic (Bolger et al., *Bioinformatics*, 2014, 30: 2114-2120), discarding reads pairs containing adapters. For libraries sequenced on the MiSeq 2×300, reads were also cropped to 150 bp. TMIseq data was further processed according to the following pipeline: First, molecular identifiers are extracted from the trimmed fastq files. For Uncut libraries the first 18 bases of read 1 represent molecular identifier 1 and the first 18 bases of read 2 represent molecular identifier 2. For Tn5_A libraries the first 18 bases of read 2 represent molecular identifier 2. For Tn5_B libraries the first 18 bases of read 1 represent molecular identifier 1. Second, reads of the Uncut library are grouped into molecular groups if their combined molecular identifiers differed by less than 5 mismatches. Third, reads with highly similar (less than 2 mismatches) molecular identifier 1 (Tn5_B) or molecular identifier 2 (Tn5_A) to the Uncut molecular groups are added into these molecular groups. Third, the AMPssembler algorithm assembles IGH transcripts from each molecular group. The program sorts the raw reads into three categories: 1.) reads derived from the 5' "end" of the amplicon. 2.) reads derived from the 3' "end", and 3.) reads which are unanchored and likely to come from some place in the middle of the molecule. Then the program creates a high-quality consensus of the ends of the amplicon using a combination of quality and abundance of each nucleotide at each position. Finally, the program reduces all of the reads into k-mers and extends one of the ends until the program reaches the other end of the amplicon or the program runs out of extensions. It then reports the completed molecule in fastq format. When multiple extensions are possible, the program always selects the extension which results in the highest-quality base being incorporated into the extension. Control data was processed as previously described (Vollmers et al., *Proc. Natl. Acad. Sci. U.S.A.*, 2013, 110: 13463-13468). To analyze molecule coverage distribution in FIG. 3B the raw reads of each molecule group were aligned to the assembled molecule using BLAST (Altschul et al., *J. Mol. Biol.*, 1990, 215: 403-410). Data was then converted to the fasta format and annotated using IgBLAST (Ye et al., *Nucleic Acids Res.*, 2013, 41: W34-40) with germline data retrieved from IMGT (Lefranc et al., *In Silico Biol.*, 2004, 4: 17-29). For FIG. 6 IGH molecules were grouped into lineages across all samples analyzed using a single linkage clustering approach and a 90% CDR3 similarity cut-off. For FIG. 1E reads were subsampled to the approximate target levels from the unprocessed fastq file pairs. The resulting subsampled files were then analyzed by the complete analysis pipeline. Further downstream analysis and visualization was done using Python/Matplotlib (Hunter, *Comput. Sci. Eng.*, 2007, 9: 90-95).

Data Access

The AMPssembler script used in the analysis of the data is available at Github at "https" followed by "://github." Followed by "com/chkcole/AMPssembler". Raw data was uploaded to the SRA under Accession SRP061676 (I1 data are identified by anonymized ID SHC1-3-1, I2 data are identified by anonymized ID BB7).

Example 1: IgH Transcript Sequencing Library Generation

Three independent full-length IgH transcript sequencing libraries have been generated according to the methods of the present disclosure.

In one example, RNA was extracted from human Peripheral Blood Mononuclear cells (PBMCs, containing antibody producing B cells). Approximately 50-101 ng of RNA was reverse transcribed using primers specific for the IgH constant region and Superscript II® reverse transcriptase (Life Technologies).

cDNA was tagged with molecular barcodes and incomplete sequencing Adapters A and B at either end using modified primers specific for the IgH V region and IgH Constant region utilizing two PCR cycles and Phusion® polymerase (Thermo Scientific). After size selection purification with SPRI beads, amplification and completion of the sequencing adapters of the tagged cDNA was carried out using primers specific to the incomplete sequencing adapter utilizing 30 PCR cycles and Platinum® Taq DNA Polymerase High Fidelity (Life Technologies).

After size selection purification with SPRI beads, the amplified cDNA was split into three aliquots. Two of the aliquots were fragmented and tagged (or "tagmented") using self-produced Tn5 enzyme loaded with oligonucleotides containing Tn5 recognition sequences and partial sequencing adapters A or B, respectively. The resulting tagmented cDNA aliquots were PCR amplified with KAPA HIFI® polymerase (Kapa Biosystems) and size selected by agarose gel extraction. The third aliquot was not tagmented.

The two tagmented aliquots and the untagmented aliquot were pooled at 1:4:4 (untagmented:A:B) ratio and sequenced on an Illumina MiSeq® sequencer 2×300 run. ~20000, 70000, and 140000 reads were generated for the uncut, B, and A libraries, respectively. A 2×300 MiSeq® sequencer run was chosen to emulate different read lengths and determine the efficiency of the protocol.

To emulate an Illumina HiSeq® sequencer 2×150 bp run, only the first 150 bp of each read were used for data analysis. The assembly pipeline generated about 3250 highly quality assembly reads ranging in length from 530 bp to 610 bp. The assembly is highly efficient, as it corresponds to a >70% success rate to assemble an IgH cDNA molecule if it is present in the uncut library and took only several minutes to complete on a standard desktop computer.

The assembly length is far longer than what a 2×150 sequencing run could generate, and is even outside the practical capability of an Illumina MiSeq® 2×300. The 2×300 runs are limited to amplicons <450 bp because the last 50 bp of the first read and 100 bp of the second read are of very low quality and therefore unusable. Further, the length of the assembled cDNAs only reflects the full length of the designed amplicon, not a limitation of the protocol. The primers were designed to capture all areas in the IgH transcript of interest, which ends up being the observed assembly length. For Illumina-based sequencing, the true limit of this method is the cluster generation of Illumina sequencers which becomes inefficient for amplicons >1000 bp.

Example 2: TMIseq

To assemble RNA molecules that exceed the sequencing length but not the cluster generation length of Illumina sequencers, TMIseq utilizes molecular identifiers and the unique characteristics of the Tn5 enzyme. RNA molecules were reverse transcribed into cDNA (using primers as shown in TABLE 1: SEQ ID NOs:1-5) and then second and third strand copies of cDNA were generated in a two cycle amplification reaction using two primer pools. The primer pools used for this two cycle reaction are (TABLE 1): 1.) The V_Leader pool containing primers specific to the Leader exons of all V segments (SEQ ID NOs:11-22) 2.) The C_long pool containing primers that bind 100 bp into the Constant regions of all Isotypes (C_long) (SEQ ID NOs:6-10). All primers in these pools feature modified 5' ends to generate a single third strand cDNA copy of each IGH RNA molecule tagged with 18 bp random molecular identifiers and partial Nextera (Illumina) sequences on both ends (Nextera_A for V_Leader, Nextera_B for C_long) (FIGS. 1A-1G). These uniquely tagged cDNAs were then amplified using two primers specific to the partial Nextera A and B sequences, respectively (e.g., SEQ ID NOs:37-38). Both primers complete their respective Nextera sequence and add a sample index while preserving the molecular identifiers. This results in a dual-indexed ~530 bp amplicon library that is Illumina-sequencing-ready. The library is then split into three aliquots.

TABLE 1

List of Primers

| | |
|---|---|
| Reverse Transcription | |
| IGHM*S | GTAGCAGGTGCCAGCTGTGTCG (SEQ ID NO: 1) |
| IGHD*S | TTTCATGGGGCCATGGTCTGTTACA (SEQ ID NO: 2) |
| IGHG*S | CCGGCCGTGGCACTCATTTACCC (SEQ ID NO: 3) |
| IGHE*S | GGAGGCAGGAGTACGTCATTTACCG (SEQ ID NO: 4) |
| IGHA*S | GTAGCAGGTGCCGTCCRCCTCC (SEQ ID NO: 5) |
| 2$^{nd}$ and 3$^{rd}$ Strand Synthesis TMIseq C_Long Pool | |
| IGHG_16N_Nextera_long | GTGGGCTCGGAGATGTGTATAAGAGACAGNNNNNNTTNNN NTTNNNNNGGGAAGTAGTCCTTGACCA (SEQ ID NO: 6) |
| IGHA_16N_Nextera_long | GTGGGCTCGGAGATGTGTATAAGAGACAGNNNNNNNTTN NNNTTNNNGGGGAAGAAGCCCTGGAC (SEQ ID NO: 7) |
| IGHE_16N_Nextera_long | GTGGGCTCGGAGATGTGTATAAGAGACAGNNNNNNTTNNN NTTNNNNNAAGTAGCCCGTGGCCAGG (SEQ ID NO: 8) |
| IGHD_16N_Nextera_long | GTGGGCTCGGAGATGTGTATAAGAGACAGNNNNNTTNNN NTTNNNNNTGGGTGGTACCCAGTTATCAA (SEQ ID NO: 9) |
| IGHM_16N_Nextera_long | GTGGGCTCGGAGATGTGTATAAGAGACAGNNNNNNNNTT NNNNTTNNGAAGGAAGTCCTGTGCGAG (SEQ ID NO: 10) |
| V_Leader Pool | |
| IGHV1/7_16N_Nextera_Leader | GTCGGCAGCGTCAGATGTGTATAAGAGACAGNTNNNNNN NNTNNNNNNNATGGACTGGACCTGGAGGDTC (SEQ ID NO: 11) |
| IGHV1_2_16N_Nextera_Leader | GTCGGCAGCGTCAGATGTGTATAAGAGACAGNNTNNNNN NNNTNNNNNNATGGCTGGAYTTGGAGGATC (SEQ ID NO: 12) |
| IGHV2_1_16N_Nextera_Leader | GTCGGCAGCGTCAGATGTGTATAAGAGACAGNNNTNNNN NNNNTNNNNNATGGACACACTTTGTTCCACGC (SEQ ID NO: 13) |
| IGHV2_2_16N_Nextera_Leader | GTCGGCAGCGTCAGATGTGTATAAGAGACAGNNNNTNNN NNNNNTNNNNATGGACACYTTTGCTMCACACT (SEQ ID NO: 14) |
| IGHV3_1_16N_Nextera_Leader | GTCGGCAGCGTCAGATGTGTATAAGAGACAGNNNNNTNN NNNNNNTNNNATGGAGTTKGGGCTGAGCTG (SEQ ID NO: 15) |
| IGHV3_3_16N_Nextera_Leader | GTCGGCAGCGTCAGATGTGTATAAGAGACAGNNNNNNTN NNNNNNNTNNATGSATTTGKSCTGAGCTGG (SEQ ID NO: 16) |
| IGHV3_4_16N_Nextera_Leader | GTCGGCAGCGTCAGATGTGTATAAGAGACAGNNNNNNNT NNNNNNNNTNATGACGGAGTTTGGGCTGAG (SEQ ID NO: 17) |
| IGHV3_5_16N_Nextera_Leader | GTCGGCAGCGTCAGATGTGTATAAGAGACAGNTNNNNNN NTNNNNNNNNATGGAACTGGGGCTCCGC (SEQ ID NO: 18) |

TABLE 1-continued

| List of Primers | |
|---|---|
| IGHV4_1_6N_Nextera_Leader | GTCGGCAGCGTCAGATGTGTATAAGAGACAGNNTNNNNN<br>NNTNNNNNNNATGAAACACCTGTGGTTCTTCCTC<br>(SEQ ID NO: 19) |
| IGHV5_1_16N_Nextera_Leader | GTCGGCAGCGTCAGATGTGTATAAGAGACAGNNNTNNNN<br>NNNTNNNNNNATGCAAGTGGGGGCCTCTC<br>(SEQ ID NO: 20) |
| IGHV5_2_16N_Nextera_Leader | GTCGGCAGCGTCAGATGTGTATAAGAGACAGNNNNTNNN<br>NNNNTNNNNNATGGGGTCAACCGCCATCC<br>(SEQ ID NO: 21) |
| IGHV6_1_6N_Nextera_Leader | GTCGGCAGCGTCAGATGTGTATAAGAGACAGNNNNNTNN<br>NNNNNTNNNNATGTCTGTCTCCTTCCTCATCT<br>(SEQ ID NO: 22) |

Control
C-short Pool

| | |
|---|---|
| IGHD_Nextera_Combinatorial | GTGGGCTCGGAGATGTGTATAAGAGACAGNNNTTNNNNN<br>NNGGAACACATCCGGAGCCT (SEQ ID NO: 23) |
| IGHM_Nextera_Combinatorial | GTGGGCTCGGAGATGTGTATAAGAGACAGNNNNNNTTNN<br>NNGAAAAGGGTTGGGGCGGAT (SEQ ID NO: 24) |
| IGHG_Nextera_Combinatorial | GTGGGCTCGGAGATGTGTATAAGAGACAGNNNTTNNNNN<br>NNAAGACCGATGGGCCCTT (SEQ ID NO: 25) |
| IGHA_Nextera_Combinatorial | GTGGGCTCGGAGATGTGTATAAGAGACAGNNNNNTTNNN<br>NNGAAGACCTTGGGGCTGGT (SEQ ID NO: 26) |
| IGHE_Nextera_Combinatorial | GTGGGCTCGGAGATGTGTATAAGAGACAGNNNTTNNNNN<br>NNGAAGACGGATGGGCTCTGT (SEQ ID NO: 27) |

V_FR1 Pool

| | |
|---|---|
| IGHV1_1_16N_Nextera_70 | GTCGGCAGCGTCAGATGTGTATAAGAGACAGNTNNNNNN<br>NNTNNNNNNNSCAGCTGGTGCAGTCTGG<br>(SEQ ID NO: 28) |
| IGHV1/3/5_16N_Nextera_70 | GTCGGCAGCGTCAGATGTGTATAAGAGACAGNNNTNNNN<br>NNNTNNNNNNGTGCAGCTGGTGGAGTCTG<br>(SEQ ID NO: 29) |
| IGHV2_16N_Nextera_70 | GTCGGCAGCGTCAGATGTGTATAAGAGACAGNNNNTNNN<br>NNNNTNNNNNTCACCTTGAAGGAGTCTGG<br>(SEQ ID NO: 30) |
| IGHV4_1_16N_Nextera_70 | GTCGGCAGCGTCAGATGTGTATAAGAGACAGNNNNTNNN<br>NNNNNTNNNNTGCAGCTGCAGGAGTCG<br>(SEQ ID NO: 31) |
| IGHV4_2_16N_Nextera_70 | GTCGGCAGCGTCAGATGTGTATAAGAGACAGNNNNNTNN<br>NNNNNNTNNNGTGCAGCTACAGCAGTGG<br>(SEQ ID NO: 32) |
| IGHV6_16N_Nextera_70 | GTCGGCAGCGTCAGATGTGTATAAGAGACAGNNNNNNTN<br>NNNNNNNTNNGTACAGCTGCAGCAGTCA<br>(SEQ ID NO: 33) |

Tn5 Oligos

| | |
|---|---|
| Tn5ME-R | [phos]CTGTCTCTTATACACATCT (SEQ ID NO: 34) |
| Tn5ME-A | TCGTCGGCAGCGTCAGATGTGTATAAGAGACAG (SEQ ID NO: 35) |
| Tn5ME-B | GTCTCGTGGGCTCGGAGATGTGTATAAGAGACAG (SEQ ID NO: 36) |
| Nextera_Primer_A_5 | AATGATACGGCGACCACCGAGATCTACAC (SEQ ID NO: 37) |
| Nextera_Primer_B_5 | CAAGCAGAAGACGGCATACGAGAT (SEQ ID NO: 38) |
| Nextera_Primer_A_3 | TCGTCGGCAGCGTCAGATG (SEQ ID NO: 39) |
| Nextera_Primer_B_3 | GTGGGCTCGGAGATGTGTAT (SEQ ID NO: 40) |
| Nextera_Primer_A_Universal | AATGATACGGCGACCACCGAGATCTACAC (SEQ ID NO: 37) |
| Nextera_Primer_B_Universal | CAAGCAGAAGACGGCATACGAGAT (SEQ ID NO: 38) |

FIGS. 1A-1G: Schematic of TMIseq Library Preparation and Data Analysis: IGH RNA is reverse transcribed and second and third strand cDNA is generated using 5 prime modified primers. After PCR amplification the amplicons are tagmented using custom loaded Tn5 enzymes. Three libraries per sample are sequenced and the resulting reads are grouped using molecular identifiers and assembled with a custom algorithm (AMPssembler).

The first and second aliquots (Tn5_A and Tn5_B) are tagmented with Tn5 enzyme loaded only with partial Nextera_A (Tn5_A) or Nextera_B (Tn5_B) oligos (see, TABLE 1, SEQ ID NOs: 34-36) and PCR amplified to complete the Nextera_A (Tn5_A) or Nextera_B (Tn5_B) sequences, respectively (FIGS. 1A-1G). At this point, Tn5_A and Tn5_B libraries are Illumina-sequencing-ready and there is no enrichment required as Illumina chemistry only sequences molecules with both complete Nextera_A and Nextera_B sequences at their ends (FIGS. 1A-1G). Therefore, Tn5_A and Tn5_B libraries produce raw read pairs in which one read is anchored by the V_Leader (Tn5_A) or C_long (Tn5_B) primers and contains one of the molecular identifiers associated with the original template molecule, whereas the other read is primed from the Nextera sequence which was introduced at a random location into the amplicon by Tn5.

The third aliquot (Uncut) is left unchanged and sequenced alongside the Tn5_A and Tn5_B libraries (FIG. 1, panels A-G) and exclusively produces raw read pairs in which both reads are anchored by V_Leader or C_long primers and contain both molecular identifiers associated with the original template molecule (FIG. 1, panels A-G).

For analysis, after quality trimming and filtering, Uncut, Tn5_A and Tn5_B read pairs containing highly similar molecular identifiers (FIG. 2) in their anchored reads are combined into IGH molecule groups. IGH molecules are then assembled from each group using AMPssembler, a custom k-mer based amplicon assembler that takes advantages of the known properties of the TMIseq protocol. Namely, the ends of the assembled sequences are defined by the anchored reads and there is only a single sequence to be assembled per IGH molecule group.

Figure 2:
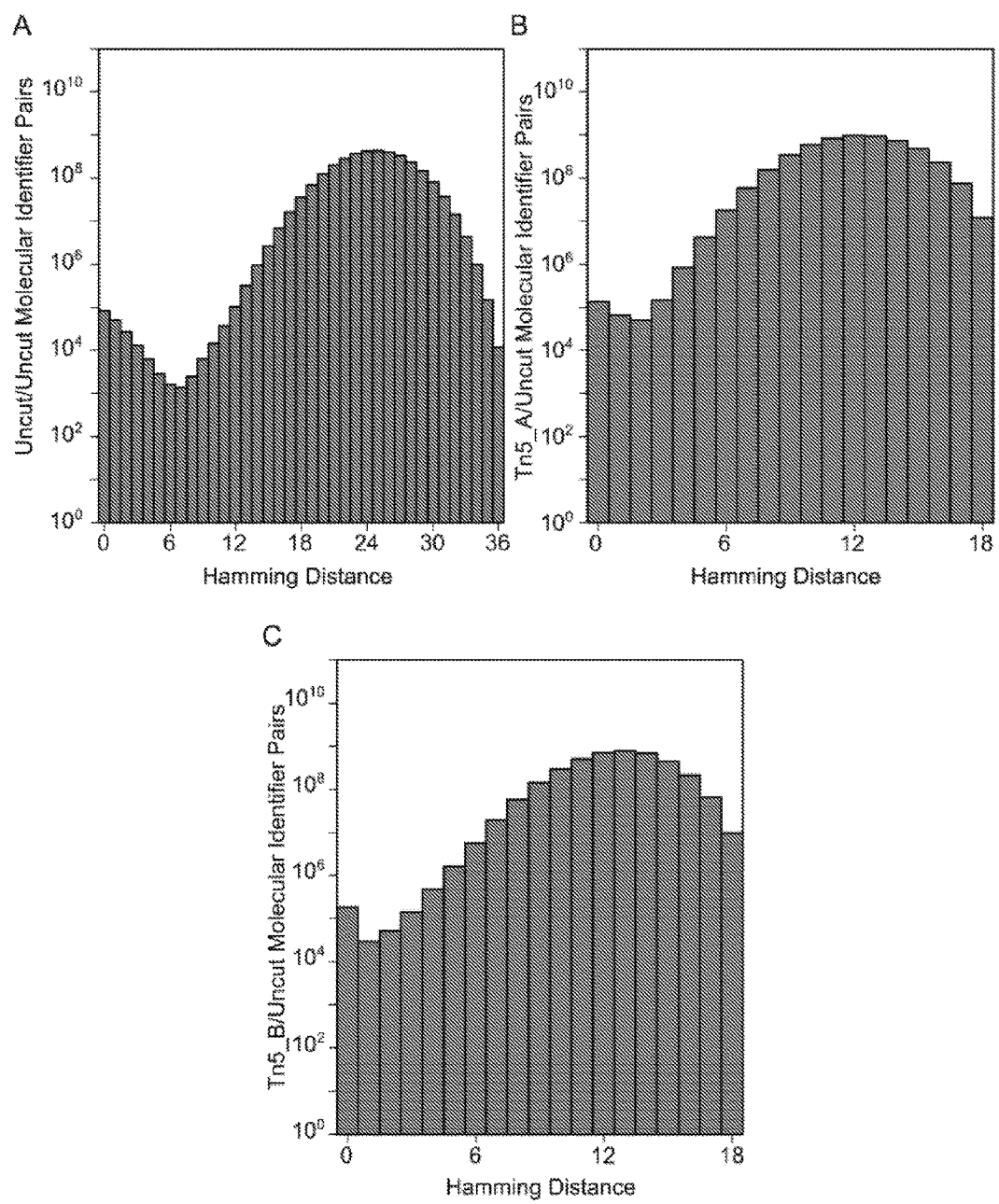
FIG. 2, panels A-C, depict data showing the determining molecular identifier similarity cut-offs for IGH molecule groups.

FIG. 2, panels A-C: Determining Molecular Identifier Similarity Cut-offs for IGH Molecule Groups. FIG. 2A) A histogram showing the Hamming Distance of the 36 bp molecular identifier (18 bp read 1+18 bp read 2) of 10,000 filtered Uncut reads to all other filtered Uncut reads (~420,000). FIG. 2B) A histogram showing the Hamming Distance of the 18 bp read 2 molecular identifier of 10,000 filtered Uncut reads to all trimmed Tn5_A reads (~500,000). FIG. 2C) A histogram showing the Hamming Distance of the 18 bp read 1 molecular identifier of 10,000 filtered Uncut reads to all trimmed Tn5_B reads (~365,000).

Example 2: Application of TMIseq to the Analysis of IGH Transcript Amplicons

To test the TMIseq protocol and data analysis, TMIseq libraries were created from two individuals (I1 and I2) from samples of PBMCs (Peripheral Blood Mononuclear Cells) which contain B cells. For I1, TMIseq Uncut, Tn5_A, and Tn5_B libraries were generated for one sample (I1 L1), and those libraries were sequenced on a MiSeq 2×300 run and truncated the resulting reads to 150 bp to model the shorter read length. The MiSeq run generated 125,200 raw reads for the I1 libraries, which yielded 120,104 quality trimmed reads. The trimmed read pairs were assembled by AMPssembler into 2779 IGH molecules. For I2, TMIseq Uncut, Tn5_A, and Tn5_B libraries were generated for 8 samples (I2 L1-L8) and those libraries were sequenced on a HiSeq3000 2×150 run. The HiSeq run generated 15,587,484 raw read pairs across the 8 I2 samples, which yielded 10,577,945 quality trimmed read pairs. These trimmed read pairs were assembled by AMPssembler into 115,108 IGH molecules (11,075-16,985 IGH molecules per library) (FIG. 3).

FIG. 3: Sequencing Run Overview. A table illustrating the numbers of sequencing reads and molecules at different stages of the analysis pipeline. (1) MiSeq forward and reverse reads were truncated to 150 bp. (2) Reads surviving Trimmomatic processing. (3) Uncut reads are filtered for reads containing Constant Region and Variable Region sequences. (4) Trimmed Tn5_A and Tn5_B reads were matched with IGH molecules using molecular identifiers. (5) IGH molecule groups are assembled using the AMPssembler algorithm. (6) Assembled IGH molecules are annotated using IgBlast.

Example 3: TMIseq Coverage Requirements

Figure 4:
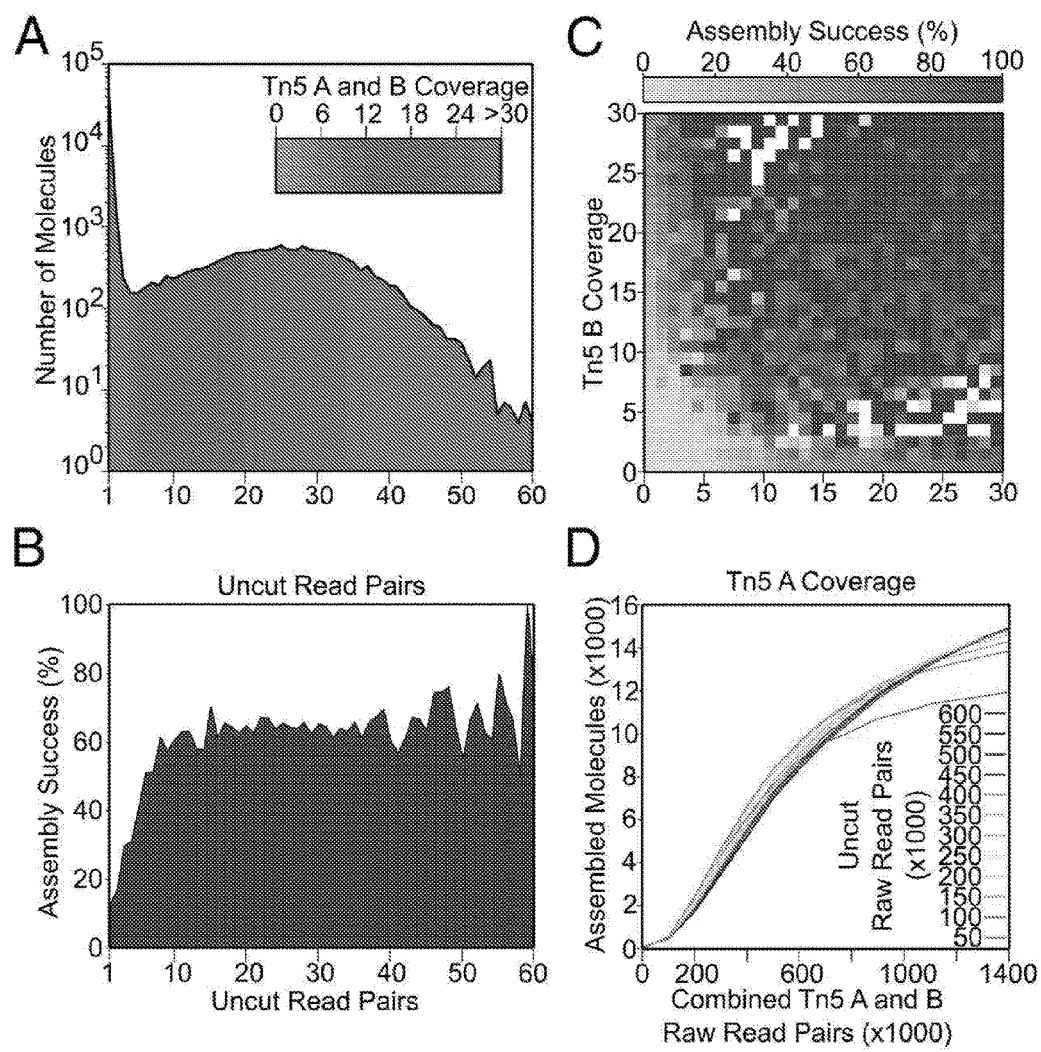
FIG. 4, panels A-D, depict data showing subassembly coverage requirements of a method according to one embodiment.

I2 L1 data was used to determine the coverage requirements to assemble IGH molecules and enable future optimization of raw read depth. Successful assembly was strongly dependent on read coverage, which itself showed a strong positive correlation between the Uncut and Tn5_A/Tn5_B libraries (FIG. 4, panels A and B). TMIseq assembly success increased from 15% for IGH molecules covered by only one Uncut read pair to 60-70% for reads covered by 5 or more Uncut read pairs (FIG. 4, panel C). With the assembly success of individual molecules being highly dependent on Tn5_A and Tn5_B coverage, reaching over 90% for IGH molecules covered by more than 40 combined Tn5_A and Tn5_B read pairs (FIG. 4, panel C).

FIG. 4, panels A-D: TMIseq Subassembly Coverage Requirements: FIG. 4, panel A) Read pair coverage for IGH molecules in the I2 L1 Uncut library is shown as a histogram. Average Combined Tn5_A and Tn5_B read coverage at increasing Uncut raw read coverage levels is shown as a gradient. FIG. 4, panel B) Average assembly success at increasing I2 L1 Uncut read coverage levels is shown. FIG. 4, panel C) Heatmap showing the correlation of assembly success and read coverage in I2 L1. Average Success percentage for Tn5_A and Tn5_B coverage combinations is shown. FIG. 4, panel D) Number of I2 L1 IGH molecules successfully assembled from increasing numbers of subsampled Uncut raw read pairs and combined Tn5_A and Tn5_B raw read pairs is plotted.

Rarefaction analysis was performed to determine the ideal coverage levels required for effective assembly. While subsampling of the Tn5_A and Tn5_B raw reads had a strong impact on the number of IGH molecules that were successfully assembled, subsampling of the Uncut raw reads had only minimal effect until the number of raw reads fell below 2-5 times the maximum number of assembled IGH molecules (FIG. 4, panel D). A good trade-off between assembled IGH molecules and raw read coverage therefore appears to be 5 Uncut raw reads and 30-40 raw reads each for Tn5_A and Tn5_B for every high abundance IGH molecule in the Uncut library. In comparison to other approaches that enable the sequencing of molecules exceeding the Illumina read length limit, TMIseq already requires far less reads per assembled molecule (Hong et al., *Genome Biol.*, 2014, 15: 517). Further, raw read requirements are likely to be lower if using a HiSeq2500, as the HiSeq3000 used in this example has a strong preference for short molecules, which resulted in ~40% of Tn5_A and Tn5_B reads to be discarded in a quality filtering step because they were too short or contained adapter sequences (FIG. 3).

Example 4: TMIseq Data Quality

Figure 5:
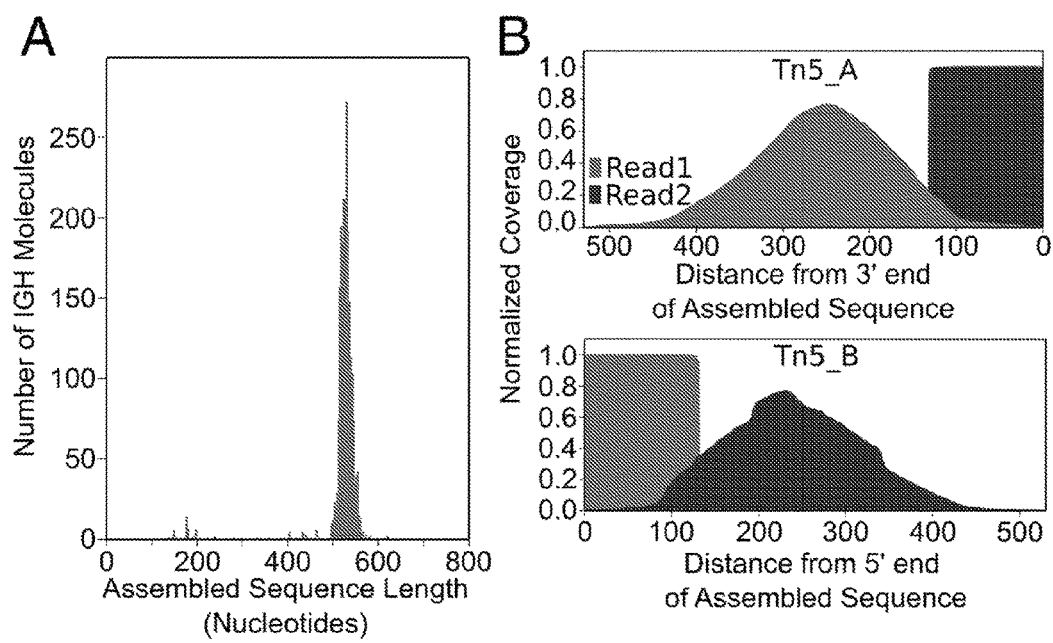
FIG. 5, panels A and B, depict data showing assembly of 530 bp IGH molecules using a method according to an embodiment of the present disclosure.

To assess TMIseq data quality and characteristics IGH molecules assembled from the I1 L1 library were analyzed. The average length of the assembled IGH molecules was 530 bp (FIG. 5, panel A) and trimmed Tn5_A and Tn5_B reads aligned to the assembled molecules in the pattern expected based on the library prep protocols (FIG. 5B). Of the 2779 assembled IGH molecules, 98% were identified as heavy chain transcript and annotated by IgBlast (Ye et al., *Nucleic Acids Res.*, 2013, 41: W34-40). These annotated IGH molecules were then compared to standard molecular-identifier based immune repertoire control data (I1 Control) derived from a biological replicate and produced using a shorter 400 bp amplicon and a 2×300 run on a MiSeq.

FIG. 5, panels A and B: TMIseq Assembles 530 bp IGH Molecules: panel A) Length distribution of I1 L1 IGH molecules assembled using TMIseq. panel B) Trimmed Tn5_A and Tn5_B reads are mapped to assembled IGH molecules using BLAST. Mapped read coverage across IGH transcripts is shown as histograms.

Figure 6:
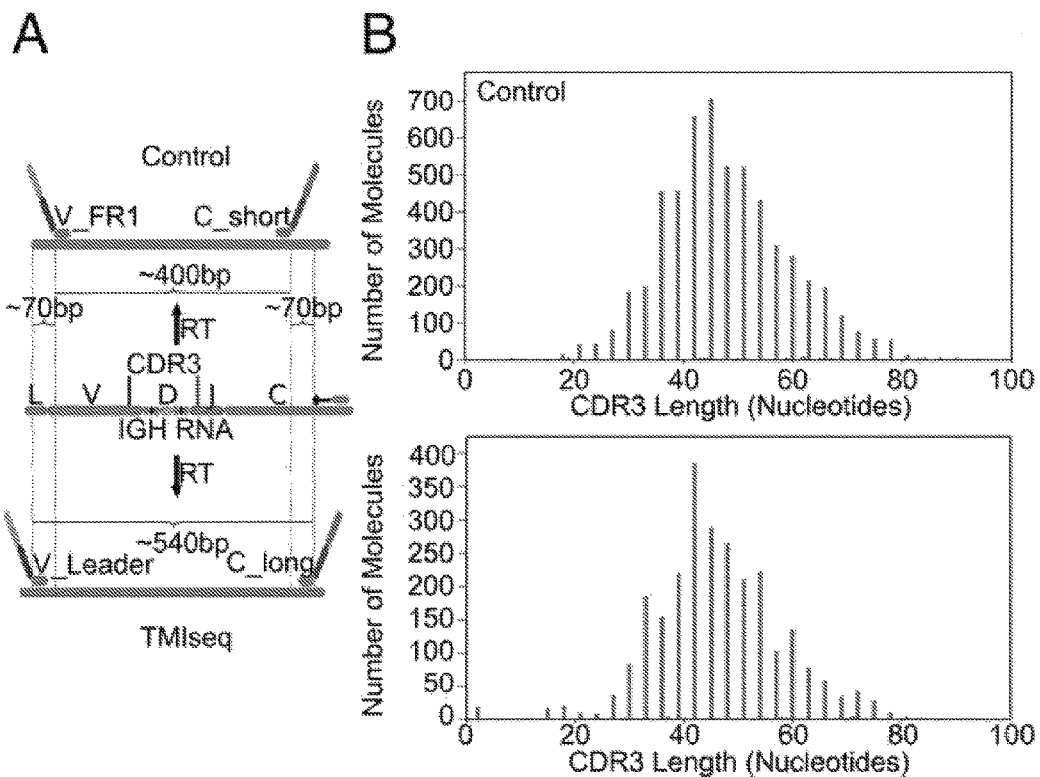
FIG. 6, panels A-D, depict data showing that mutation data for a method according to one embodiment is equivalent to control libraries.
Figure 6:
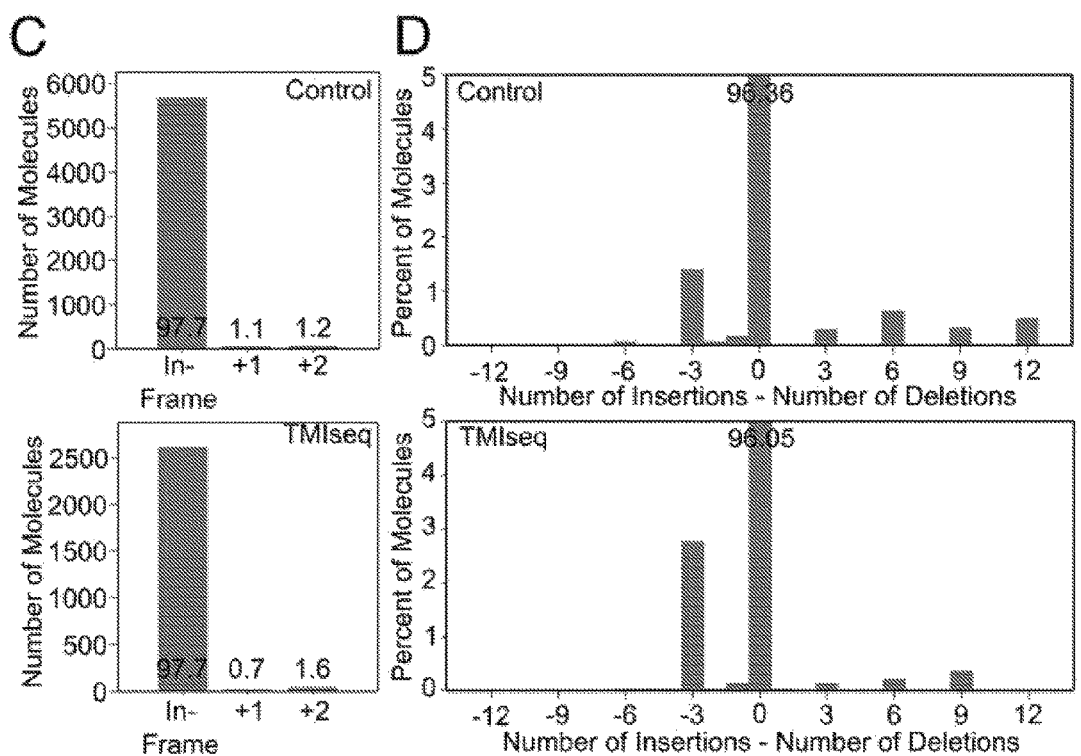

FIG. 6, panels A-D: TMIseq Mutations Data Equivalent to Control Libraries: FIG. 6, panel A) Schematic of Primer positioning for second and third strand synthesis in TMIseq and control Libraries. Control and TMIseq sequences are compared for CDR3 length distribution (panel B), CDR3 translation frame (panel C), shift in frame produced by indels (panel D).

To assess base-exchange errors, IgD sequences were examined, which are thought to be expressed almost exclusively by naïve B cells. The vast majority of sequenced IgD sequences should therefore be not mutated. Indeed, most IgD sequences were not mutated: 95.16% of IgD sequences in the I1 L1 TMIseq library and 93.6% of IgD sequences in the I1 Control library showed >99% identity to reference. The percentage of mutated IgD sequences was comparable between TMIseq and error-corrected control libraries.

Rates of artificial insertion and deletions of the TMIseq protocol were examined, which, as it relies on computational assembly of sequences, might be prone to generate these kinds of errors. First, the observed CDR3 lengths and potential frame-shifts in the variable region were analyzed. Lengths of the CDR3s, which is the result of the random recombination of V, D, and J segments and the addition of quasi-random P and N nucleotides, are expected to occur in steps of three to maintain the reading frame of the antibody heavy chain transcript. Second, indels occurring in the rest of the Variable region were analyzed. Indels in the variable region should occur in multiples of three to result in the in the addition or loss of whole amino acids, while maintaining the reading frame of the transcripts. It was found that the rates of out-of-frame CDR3 (FIG. 6, panels B and C) and frame-shift events in the rest of Variable region (FIG. 6, panel D) were very similar between I1 L1 TMIseq and I1 Control libraries. Together, this confirmed that the error rate generated by the TMIseq is equivalent to the rates of the error-corrected control protocol.

Example 5: Variable and Constant Region Coverage by IGH Amplicon and TMIseq

Figure 7:
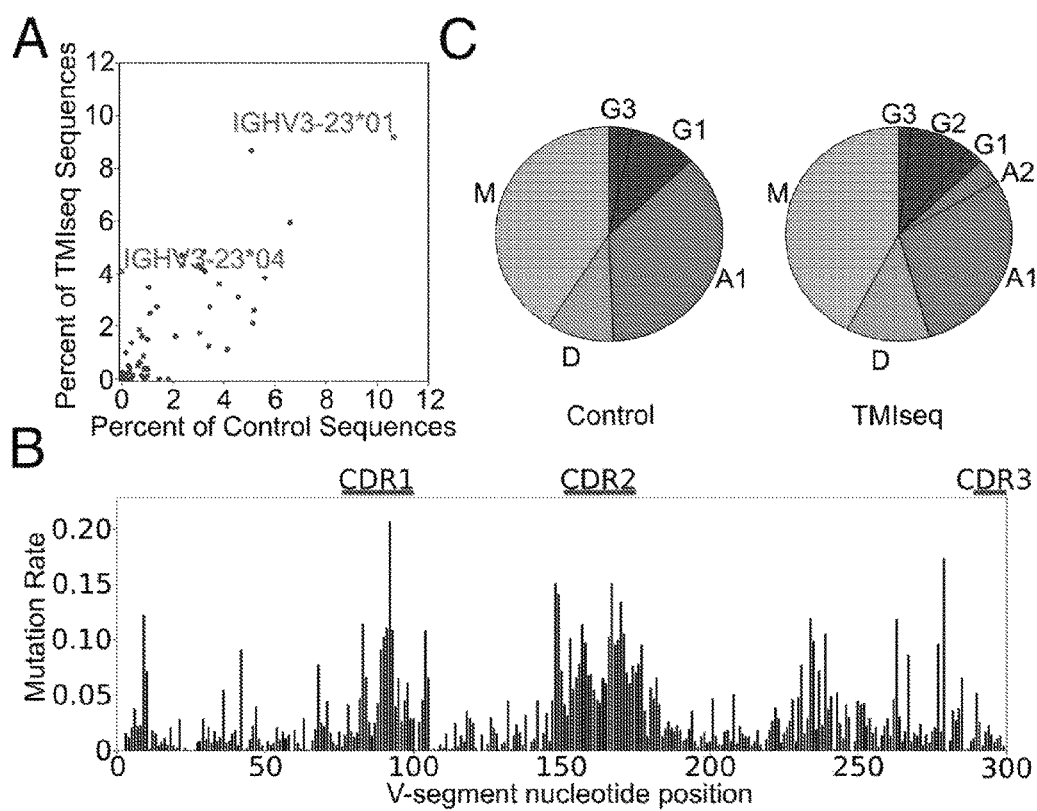
FIG. 7, panels A-C, depict data showing differentiation of V segments and isotypes using a method according to an embodiment of the present disclosure.

The increased sequencing length made possible by TMIseq enabled the creation of a longer amplicon by priming in the Leader exon and 100 bp into the Constant region. Priming in the Leader exon, which is not included in the final antibody protein, allowed the reading of every base of the Variable region without it being covered by a possibly mismatching primer and therefore modified. This enabled the unique identification of all V segment alleles. In contrast to the I1 Control library, the I1 L1 TMIseq library was able to identify the V segment allele IGHV3-23*04 that differs from the more common IGHV3-23*01 allele by a single base in the first 20 bp of the segment (FIG. 7, panel A). Additionally, priming in the Leader exon enables the identification of mutation hot spots in the entire Variable region, including potential hot spots in the first 20 bases of the IGHV3 segment family (FIG. 7, panel B).

FIG. 7, panels A-C: TMIseq can Differentiate All V Segments and Isotypes: FIG. 7, panels A and B) Control and TMIseq sequences are compared for perfectly matched V segment usage in a scatter plot (FIG. 7, panel A), and Isotype usage in a pie chart (FIG. 7, panel B). FIG. 7, panel C) Mutation rate across the entire V segment averaged across all IGH molecules using V segments of the IGHV3 family.

On the other end of the amplicon, priming 100 bp into the Constant regions creates an amplicon that contains enough distinct base positions to not only distinguish isotypes like IgM and IgG, but isotype subtypes like IgG1 and IgG3. Indeed, in contrast to the I1 Control Library, the I1 L1 TMIseq library differentiates isotype subtypes including IgG1, IgG2, and IgG3 as well as IgA1 and IgA2 (FIG. 7, panel C). While IgG4 and IgE, which are essential for allergy research, were detected at very low levels in the data, this is likely due to the low sequencing depth and their naturally low levels in a mix of IGH transcripts.

To test the data for obvious recurring assembly artifacts and contaminations, IGH molecules derived from all I1 and I2 libraries were compared. Similar to what was previously shown for standard immune repertoire data (Vollmers et al., Proc. Natl. Acad. Sci. U.S.A., 2013, 110: 13463-13468), IGH molecule lineages derived from I1 and I2 samples were shared at high levels between the samples of an individual, yet only at very low levels between individuals (FIG. 8), which confirmed the absence of rampant cross contamination and assembly artifacts.

Figure 8:
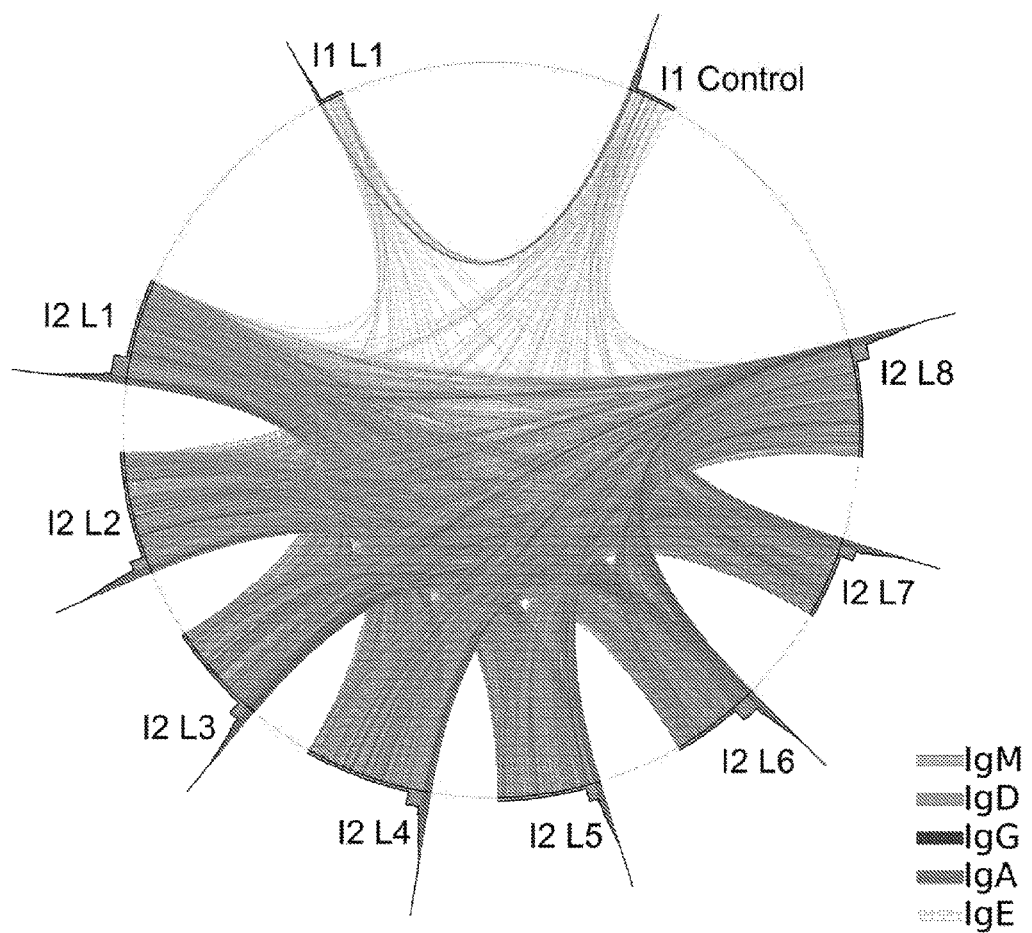
FIG. 8 illustrates that data generated using a method according to one embodiment can identify clonal IGH lineages.

FIG. 8: TMIseq Data Identifies Clonal IGH Lineages: Visualization of IGH molecule lineages shared between samples. IGH molecule lineages of each sample are plotted on the circumference of the circle, with the area representing abundance of the respective lineages (logarithmic) and the color representing isotype. IGH molecule lineages present in two time points are connected with lines colored according to their isotype.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing a nucleic acid library, comprising:

combining primers and template nucleic acid strands under conditions in which the primers are extended to produce primer extension products;

tagging the ends of the primer extension products to produce tagged extension products, wherein the tagging comprises:

adding a first sequencing adapter to a first end of the primer extension products; and adding a second sequencing adapter to a second end of the primer extension products opposite the first end, wherein the nucleic acid sequences of the first and second sequencing adapters are different;

contacting a first aliquot of the tagged extension products with a first transposome comprising a transposon that comprises all or a portion of the second sequencing adapter, to produce tagged extension product fragments comprising the first end and a shortened end comprising all or a portion of the second sequencing adapter; and contacting a second aliquot of the tagged extension products with a second transposome comprising a transposon that comprises all or a portion of the first sequencing adapter, to produce tagged extension product fragments comprising the second end and a shortened end comprising all or a portion of the first sequencing adapter.

2. The method according to claim 1, wherein tagging the ends of the primer extension products comprises amplifying the primer extension products using an amplification primer pair comprising:

a first amplification primer that comprises a 3' hybridization region and a 5' region comprising all or a portion of the first sequencing adapter; and a second amplification primer that comprises a 3' hybridization region and a 5' region comprising all or a portion of the second sequencing adapter.

3. The method according to claim 2, wherein the first and second amplification primers comprise only a portion of the first and second sequencing adapters, respectively, and wherein tagging the ends of the primer extension products further comprises amplifying the amplicons generated using the first and second primers with an amplification primer pair comprising:

a third amplification primer that comprises a 3' hybridization region and a 5' region comprising the remaining portion of the first sequencing adapter; and a fourth amplification primer that comprises a 3' hybridization region and a 5' region comprising the remaining portion of the second sequencing adapter.

4. The method according to claim 1, further comprising sequencing the tagged extension product fragments of the first aliquot, the tagged extension product fragments of the second aliquot, and an aliquot of the tagged extension products.

5. The method according to claim 4, further comprising assembling sequencing reads produced during the sequencing to determine the sequences of the template nucleic acids strands.

6. The method according to claim 1, wherein the first and second transposomes comprise a transposase independently selected from: a Tn5 transposase, a Tn7 transposase, and a Mu transposase.

7. The method according to claim 1, wherein the template nucleic acid strand is a template ribonucleic acid (RNA).

8. The method according to claim 7, wherein the template RNA is a template mRNA.

9. The method according to claim 8, wherein the template mRNA encodes an immunoglobulin.

10. The method according to claim 1, wherein the template nucleic acid strand is a template deoxyribonucleic acid (DNA) strand.

11. The method according to claim 10, wherein the template DNA strand is a template genomic DNA strand.

* * * * *